(12) United States Patent
Huang et al.

(10) Patent No.: US 7,390,780 B2
(45) Date of Patent: Jun. 24, 2008

(54) GENE DELIVERY MEDIATED BY LIPOSOME-DNA COMPLEX WITH CLEAVABLE PEG SURFACE MODIFICATION

(75) Inventors: Shi-Kun Huang, Castro Valley, CA (US); Samuel Zalipsky, Redwood City, CA (US)

(73) Assignee: Alza Corporation, Mountain View, CA (US)

( * ) Notice: Subject to any disclaimer, the term of this patent is extended or adjusted under 35 U.S.C. 154(b) by 397 days.

(21) Appl. No.: 10/993,798

(22) Filed: Nov. 19, 2004

(65) Prior Publication Data

US 2005/0170508 A1 Aug. 4, 2005

Related U.S. Application Data

(63) Continuation-in-part of application No. 10/371,169, filed on Feb. 21, 2003, now Pat. No. 6,849,270, which is a continuation of application No. 09/982,336, filed on Oct. 15, 2001, now Pat. No. 6,605,299, which is a continuation of application No. 09/556,056, filed on Apr. 21, 2000, now Pat. No. 6,342,244, application No. 10/993,798, filed on Nov. 19, 2004, which is a continuation-in-part of application No. 09/685,940, filed on Oct. 10, 2000, now Pat. No. 6,974,589.

(60) Provisional application No. 60/158,693, filed on Oct. 8, 1999, provisional application No. 60/130,897, filed on Apr. 23, 1999, provisional application No. 60/524,172, filed on Nov. 21, 2003.

(51) Int. Cl.
*A01N 61/00* (2006.01)
*A61K 31/70* (2006.01)
*C12Q 1/70* (2006.01)
*C12Q 1/68* (2006.01)
*C07H 21/04* (2006.01)

(52) U.S. Cl. ............... 514/1; 514/44; 435/5; 435/6; 536/23.1

(58) Field of Classification Search .............. 514/1, 514/44; 435/5, 6; 536/23.1
See application file for complete search history.

(56) References Cited

U.S. PATENT DOCUMENTS

| | | |
|---|---|---|
| 5,395,619 A | 3/1995 | Zalipsky et al. |
| 5,631,018 A | 5/1997 | Zalipsky et al. |
| 5,668,108 A | 9/1997 | Capon et al. |
| 5,851,818 A | 12/1998 | Huang et al. |

(Continued)

FOREIGN PATENT DOCUMENTS

WO WO 97/07784 A2 3/1997

(Continued)

OTHER PUBLICATIONS

Allen, T. et al., *Biochimica et Biophysica Acta* 1237:99-108, 1995.

(Continued)

*Primary Examiner*—Jezia Riley
(74) *Attorney, Agent, or Firm*—Michael J. Atkins

(57) ABSTRACT

A liposome composition and method for delivery of a nucleic acid in vivo or ex vivo is described. The liposomes in the composition are comprised of (i) a cationic lipid and (ii) a lipid joined to a hydrophilic polymer by a releasable linkage. The liposomes are associated with a nucleic acid for delivery to a cell.

21 Claims, 13 Drawing Sheets

U.S. PATENT DOCUMENTS

| | | | |
|---|---|---|---|
| 6,043,094 | A | 3/2000 | Martin et al. |
| 6,133,026 | A * | 10/2000 | Huang et al. ............. 435/320.1 |
| 6,180,134 | B1 | 1/2001 | Zalipsky et al. |
| 2003/0031704 | A1 | 2/2003 | Huang et al. |

OTHER PUBLICATIONS

Brois, S. et al., *J. Amer. Chem. Soc.* 92(26), 7629-7631, 1970.
Felgner, P. et al., *Proc. Natl. Acad. Sci. USA* 84:7413-7417, 1987.
Gabizon, A. et al., *Bioconjugate Chem.* 10:289-298, 1999.
Grice, R. and Owen, L., *J. Chem. Soc.*, pp. 1947-1954, 1963.
Guo, L. et al., *J. Liposome Research* 3(1):51-70, 1993.
Kaneko, T. et al., *Bioconjugate Chemistry* 2(3):133-141, 1991.
Kirpotin, D. et al., *FEBS Letters* 388:115-118, 1996.
Martin, F., *Specialized Drug Delivery Systems-Manufacturing and Production Technology*, Tyle Ed., Marcel Dekker, New York, pp. 267-316, 1990.
Morishita, R. et al., *J. Clin. Invest.* 91:2580-2585, 1993.
Mulligan, R., *Science* 260:926-932, 1993.
Saikawa, Y. et al., *Biochemistry* 34:9951-9961, 1995.
Szoka, F., *Ann. Rev. Biophys. Bioeng.* 9:467-508, 1980.
Zalipsky, S., *Stealth Liposomes*, Lasic and Martin Eds., Chapter 9 pp. 93-102, CRC Press, Boca Raton, FL, 1995.
Zalipsky, S. et al., *Biotechnology and Applied Biochemistry* 15:100-114, 1992.
Zalipsky, S. et al., *Bioconj. Chem.* 10(5):703-707, 1999.
Zalipsky, S. et al., *Bioconj. Chem.* 6(6):705-708, 1995.
Zalipsky, S. et al., *Eur. Polymer J.* 19(12):1177-1183, 1983.
Zalipsky, S., *Bioconj. Chem.* 4(4):296-299, 1993.
Zalipsky, S. et al., *FEBS Letters* 353:71-74, 1994.
Huang, S. et al., *Molecular Therapy* 3(5):S9-S11, 2001.

* cited by examiner

GENE DELIVERY MEDIATED BY LIPOSOME-DNA COMPLEX WITH CLEAVABLE PEG SURFACE MODIFICATION

This application claims priority to U.S. provisional application Ser. No. 60/524,172, filed Nov. 21, 2003. This application is also a continuation-in-part of U.S. utility application Ser. No. 10/371,169, filed Feb. 21, 2003 now U.S. Pat. No. 6,849,270, now allowed, which is a continuation of U.S. utility application Ser. No. 09/982,336, filed Oct. 15, 2001, now U.S. Pat. No. 6,605,299, which is a continuation of U.S. utility application Ser. No. 09/556,056, filed Apr. 21, 2000, now U.S. Pat. No. 6,342,244, which claims the benefit of U.S. provisional application Ser. No. 60/130,897, filed Apr. 23, 1999. This application is also a continuation-in-part of U.S. utility application Ser. No. 09/685,940, filed Oct. 10, 2000 now U.S. Pat. No. 6,974,589, which claims the benefit of U.S. provisional application Ser. No. 60/158,693, filed Oct. 8, 1999. Each of these documents is incorporated is herein by reference in its entirety.

FIELD OF THE INVENTION

The present invention relates to liposome compositions for delivery of nucleic acids. More particularly, the invention relates to a liposome composition that includes a cationic lipid and a surface coating of releasable hydrophilic polymer chains for administration of nucleic acids.

BACKGROUND OF THE INVENTION

A variety of methods have been developed to facilitate the transfer of genetic material into specific cells. These methods are useful for both in vivo or ex vivo gene transfer. In the former, a gene is directly introduced (intravenously, intraperitoneally, aerosol, etc.) into a subject. In ex vivo (or in vitro) gene transfer, the gene is introduced into cells after removal of the cells from specific tissue of an individual. The transfected cells are then introduced back into the subject.

Delivery systems for achieving in vivo and ex vivo gene therapy include viral vectors, such as retroviral vectors or adenovirus vectors, microinjection, electroporation, protoplast fusion, calcium phosphate, and liposomes (Felgner, J., et al., *Proc. Natl. Acad. Sci. USA* 84:7413-7417 (1987); Mulligan, R. S., *Science* 260:926-932 (1993); Morishita, R., et al., *J. Clin. Invest.* 91:2580-2585 (1993)).

Delivery of genetic material to cells using liposomal carriers has been widely studied. It is generally understood that liposome vesicles are taken up by cells via endocytosis and enter the lysosomal degradation pathway. Thus, some effort towards designing liposomes that avoid degradation has been made.

The use of cationic lipids, e.g., derivatives of glycolipids with a positively charged ammonium or sulfonium ion-containing headgroup, for delivery of negatively-charged biomolecules, such as oligonucleotides and DNA fragments, as a liposome lipid bilayer component is widely reported. The positively-charged headgroup of the lipid interacts with the negatively-charged cell surface, facilitating contact and delivery of the biomolecule to the cell. The positive charge of the cationic lipid is further important for nucleic acid complexation.

However, systemic administration of such cationic liposome/nucleic acid complexes leads to their facile entrapment in the lung. This lung localization is caused by the strong positive surface charge of the conventional cationic complexes. In vivo gene expression of the conventional cationic complexes with reporter gene has been documented in the lung, heart, liver, kidney, and spleen following intravenous administration. However, morphological examination indicates that the majority of the expression is in endothelial cells lining the blood vessels in the lung. A potential explanation for this observation is that the lung is the first organ that cationic liposome/nucleic acid complexes encounter after intravenous injection. Additionally, there is a large surface area of endothelial cells in the lung, which provides a readily accessible target for the cationic liposome/nucleic acid complexes.

Although early results were encouraging, intravenous injection of simple cationic liposomes has not proved useful for the delivery of genes to systemic sites of disease (such as solid tumors other than lung tumors) or to the desired sites for clinically relevant gene expression (such as p53 or HSV-tk). Cationic liposomes are cleared too rapidly, and present a host of safety concerns.

In addition, tumor cell direct targeting is much more challenging than angiogenic endothelial cell targeting. Liposome/DNA complexes access angiogenic endothelial cells of tumor vasculature relatively easily, since the cells are directly exposed in the blood compartment. For targeting of tumor cells, liposome/DNA complexes need to extravasate through the leaky tumor blood vessels and then can reach tumor cells. Thus the complex stability, size, surface charge, blood circulation time, and transfection efficiency of complexes are all factors for tumor cell transfection and expression.

SUMMARY OF THE INVENTION

Accordingly, it is an object of the invention to provide a composition for systemic delivery of a nucleic acid to a cell.

It is another object of the invention to provide a liposome comprising a cationic lipid and a lipid derivatized with a releasable hydrophilic polymer. The liposome is complexed with an associated nucleic acid for subsequent delivery of the nucleic acid to a cell or tissue.

Accordingly, in one aspect, the invention includes a composition for administration of a nucleic acid, comprising liposomes comprised of (i) a cationic lipid and (ii) a vesicle-forming lipid derivatized with a hydrophilic polymer, where the hydrophilic polymer is covalently linked to the vesicle-forming lipid by a releasable linkage. In one embodiment, the vesicle-forming lipid is a compound having the general structure:

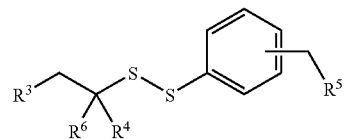

wherein $R^3$ is a hydrophilic polymer comprising a linkage for attachment to the releasable linkage; $R^4$ is selected from the group consisting of H, alkyl and aryl; $R^5$ is selected from the group consisting of $O(C=O)R^7$, $S(C=O)R^7$, and $O(C=S)R^7$; $R^7$ is the vesicle-forming lipid; and $R^6$ is selected from the group consisting of H, alkyl and aryl; and where orientation of $CH_2-R^5$ is selected from the ortho position and the para position. In one embodiment, the releasable linkage is a dithiobenzyl moiety.

In one embodiment, $R^4$ is an amine-containing lipid. The amine-containing lipid, in one embodiment, comprises either a single hydrocarbon tail or a double hydrocarbon tail. In another embodiment, the amine-containing lipid is a phospholipid having a double hydrocarbon tail.

In another embodiment, $R^4$ and $R^6$ are alkyls.

The moiety $R^3$, in one embodiment, is selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

In one embodiment, $R^3$ is polyethyleneglycol. In another embodiment, $R^6$ is H and $R^4$ is $CH_3$ or $C_2H_5$. In a preferred embodiment, $R^3$ is polyethyleneglycol, $R^6$ is H and $R^4$ is $CH_3$ or $C_2H_5$.

The cationic lipid, in one embodiment, is selected from the group consisting of dimethyldioctadecylammonium (DDAB), 1,2-diolelyloxy-3-(trimethylamino)propane (DOTAP), N-[1-(2,3,-dioleyloxy)propyl]-N,N-dimethyl-N-hydroxyethylammonium bromide (DORIE), N-[1-(2,3-dioleyloxy)propyl]-N,N,N-trimethylammonium chloride (DOTMA), dioleoylphosphatidylethanolamine (DOPE), and 3β[N-(N',N'-dimethylaminoethane)carbamoyl]cholesterol (DC-Chol).

In another embodiment, the liposome further comprises cholesterol.

It will be appreciated that the liposomes, in addition to being associated with a nucleic acid, can further include a therapeutic compound entrapped in the liposomes. The nucleic acid can be entrapped in at least a portion of the liposomes or can be externally associated with the liposomes. The nucleic acid can be DNA, RNA, fragments thereof, a plasmid, or a DNA or RNA oligonucleotide. The nucleic acid may encode a protein selected from the group consisting of Factor VIII, cytokines, p53, and HSV-tk.

In another embodiment, the liposomes further include a ligand for targeting the liposomes to a target site. Typically, the ligand is covalently attached to a distal end of the hydrophilic polymer $R^3$ on the compound. In one embodiment, the ligand has binding affinity for endothelial tumor cells for internalization by such cells. Exemplary ligands include ligands suitable for binding to the following receptors: receptor for a c-erbB-2 protein product of the HER2/neu oncogene, epidermal growth factor (EGF) receptor, basic fibroblast growth factor (basic FGF) receptor, vascular endothelial growth factor receptor, E-selectin receptor, L-selectin receptor, P-selectin receptor, folate receptor, CD4 receptor, CD19 receptor, αβ integrin receptors, and chemokine receptors. In preferred embodiment, the ligand is selected from her2, FGF, folate, and E-selectin. It will be appreciated that the liposomes can include more than one type of ligand.

These and other objects and features of the invention will be more fully appreciated when the following detailed description of the invention is read in conjunction with the accompanying drawings.

DETAILED DESCRIPTION OF THE INVENTION

I. Definitions

Figure 1:
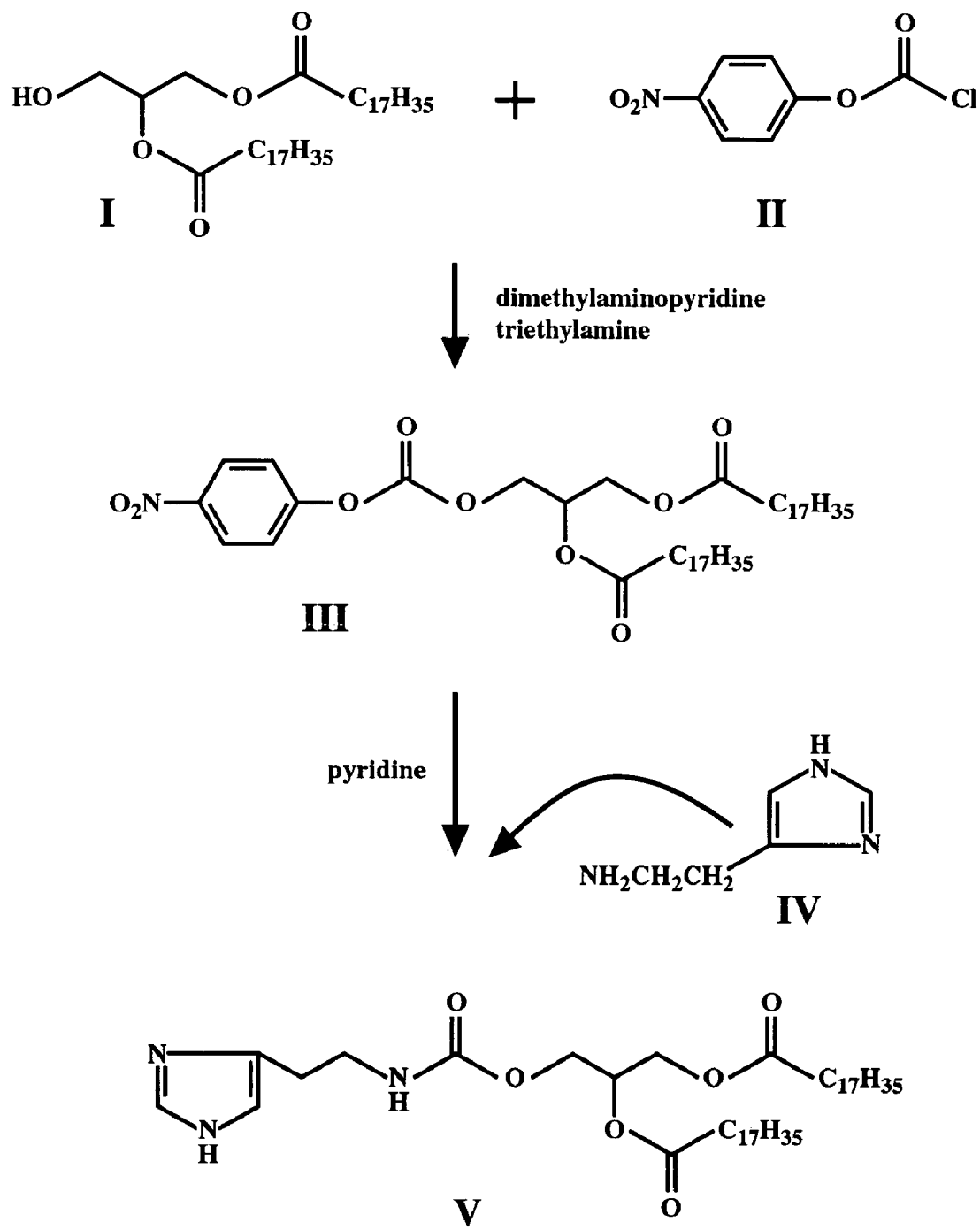
FIG. 1 shows a synthetic scheme for the preparation of a neutral cationic lipid in accordance with the invention having a carbamate linkage and an imidazole "Z" group.

The terms below have the following meanings unless indicated otherwise.

As used herein, a "cationic" lipid is one having a positive ionic character. Exemplary cationic lipids include dimethyldioctadecylammonium (DDAB), 1,2-diolelyloxy-3-(trimethylamino)propane (DOTAP), N-[1-(2,3,-dioleyloxy)propyl]-N,N-dimethyl-N-hydroxyethylammonium bromide (DORIE), N-[1-(2,3-dioleyloxy)propyl]-N,N,N-trimethylammonium chloride (DOTMA), dioleoylphosphatidylethanolamine (DOPE), and 3β[N-(N',N'-dimethylaminoethane) carbamoyl] cholesterol (DC-Chol).

A "charged" lipid is one having a positive or negative charge, having ionic character.

"Vesicle-forming lipids" refers to amphipathic lipids which have hydrophobic and polar head group moieties, and which can form spontaneously into bilayer vesicles in water, as exemplified by phospholipids, or are stably incorporated into lipid bilayers, with the hydrophobic moiety in contact with the interior, hydrophobic region of the bilayer membrane, and the polar head group moiety oriented toward the exterior, polar surface of the membrane. The vesicle-forming lipids of this type typically include one or two hydrophobic acyl hydrocarbon chains or a steroid group, and may contain a chemically reactive group, such as an amine, acid, ester, aldehyde or alcohol, at the polar head group. Included in this class are the phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14-22 carbon atoms in length, and have varying degrees of unsaturation. Also included within the scope of the term "vesicle-forming lipids" are glycolipids, such as cerebrosides and gangliosides, and sterols, such as cholesterol.

"Alkyl" refers to a fully saturated monovalent radical containing carbon and hydrogen, and which may be branched or a straight chain. Examples of alkyl groups are methyl, ethyl, n-butyl, t-butyl, n-heptyl, and isopropyl. "Lower alkyl" refers to an alkyl radical of one to six carbon atoms, as exemplified by methyl, ethyl, n-butyl, i-butyl, t-butyl, isoamyl, n-pentyl, and isopentyl.

"Alkenyl" refers to monovalent radical containing carbon and hydrogen, which may be branched or a straight chain, and which contains one or more double bonds.

"Hydrophilic polymer" as used herein refers to a polymer having moieties soluble in water, which lend to the polymer some degree of water solubility at room temperature. Exemplary hydrophilic polymers include polyvinylpyrrolidone, polyvinylmethylether, polymethyloxazoline, polyethyloxazoline, polyhydroxypropyloxazoline, polyhydroxypropylmethacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers of the above-recited polymers, and polyethyleneoxide-polypropylene oxide copolymers. Properties and reactions with many of these polymers are described in U.S. Pat. Nos. 5,395,619 and 5,631,018.

"Polymer comprising a reactive functional group" or "polymer comprising a linkage for attachment" refers to a polymer that has been modified, typically but not necessarily, at a terminal end moiety for reaction with another compound to form a covalent linkage. Reaction schemes to functionalize a polymer to have such a reactive functional group of moiety are readily determined by those of skill in the art and/or have been described, for example in U.S. Pat. No. 5,613,018 or by Zalipsky et al., in for example, *Eur. Polymer. J.*, 19(12):1177-1183 (1983); *Bioconj. Chem.*, 4(4):296-299 (1993).

"Fast-cleavable PEG" or "PEG-H-DTB-lipid" refer to an mPEG-DTB-lipid where $R^4$ and $R^6$ (see structure in Section IIB below) are hydrogen.

"Slow-cleavable PEG" or "PEG-Me-DTB-lipid" refer to an mPEG-DTB-lipid where the dithiobenzyl moiety is hindered by attachment of an alkyl moiety at $R^4$ and/or $R^6$ (see structure in Section IIB below).

An "aliphatic disulfide" linkage intends a linkage of the form R'—S—S—R", where R' and R" are linear or branched alkyl chains that may be further substituted.

Abbreviations: PEG: polyethylene glycol; mPEG: methoxy-terminated polyethylene glycol; Chol: cholesterol; PC: phosphatidyl choline; PHPC: partially hydrogenated phosphatidyl choline; PHEPC: partially hydrogenated egg phosphatidyl choline; PHSPC: partially hydrogenated soy phosphatidyl choline; DSPE: distearoyl phosphatidyl ethanolamine; APD: 1-amino-2,3-propanediol; DTPA: diethylenetetramine pentaacetic acid; Bn: benzyl; NCL: neutral cationic liposome; FGF: fibroblast growth factor; HDSG: histamine distearoyl glycerol; DOTAP: 1,2-diolelyloxy-3-(trimethylamino)propane; DORIE: N-[1-(2,3,-dioleyloxy)propyl]-N,N-dimethyl-N-hydroxyethylammonium bromide; DOTMA: N-[1-(2,3-dioleyloxy)propyl]-N,N,N-trimethylammonium chloride; DC-Chol:3β[N-(N',N'-dimethylaminoethane)carbamoyl]cholesterol; DTB: dithiobenzyl; FC-PEG: fast-cleavable PEG; SC-PEG: slow-cleavable PEG; DDAB: dimethyldioctadecylammonium; GC33: $N^2$-[$N^2,N^5$-bis(3-aminopropyl)-L-ormithyl]-N,N-dioctadecyl-L-glutamine tetrahydrotrifluoroacetate; EtDTB, ethyldithiobenzyl; DOPE, dioleoyl phosphatidylethanolamine.

II. Liposome Components

In one aspect, the invention includes a liposome composition comprised of liposomes and a nucleic acid. The liposomes are of a "cationic lipid" and a lipid derivatized with a hydrophilic polymer through a releasable bond. These liposome components will now be described.

A. Cationic Lipid

The cationic included in the liposomes of the present invention is generally a vesicle-forming lipid. In a preferred embodiment, the liposomes are comprise between about 20-80 mole percent cationic lipids. The cationic vesicle-forming lipid is one whose polar head group with a net positive charge, at the operational pH, e.g., pH 4-9. Typical examples include phospholipids, such as phosphatidylethanolamine, whose polar head groups are derivatized with a positive moiety, e.g., lysine, as illustrated, for example, for the lipid DOPE derivatized with L-lysine (LYS-DOPE) (Guo, et al., 1993). Also included in this class are the glycolipids, such as cerebrosides and gangliosides having a cationic polar head-group.

Another cationic vesicle-forming lipid which may be employed is cholesterol amine and related cationic sterols. Exemplary cationic lipids include 1,2-diolelyloxy-3-(trimethylamino)propane (DOTAP); N-[1-(2,3,-ditetradecyloxy) propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3β[N-(N',N'-dimethylaminoethane)carbamoly]cholesterol (DC-Chol); and dimethyldioctadecylammonium (DDAB). In a preferred embodiment, the cationic lipid is 1,2-diolelyloxy-3-(trimethylamino)propane (DOTAP).

In another embodiment, the cationic lipid may be a neutral cationic lipid, that is, a lipid that at physiologic pH of 7.4 is predominantly, e.g., greater than 50%, neutral in charge but at a selected pH value less than physiologic pH tends to have a positive charge. Such neutral cationic lipids are represented by the structure shown below:

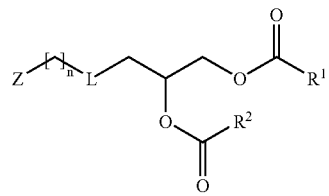

where each of $R^1$ and $R^2$ is an alkyl or alkenyl chain having between 8-24 carbon atoms; n=0-20, preferably n=1-20, and in a preferred embodiment is between 1-10; L is selected from the group consisting of (i) —X—(C=O)—Y—, (ii) —X—(C=O)—, and (iii) —X—, where X and Y are independently selected from oxygen, NH and a direct bond; and Z is a weakly basic moiety that has a pK of less than 7.4 and greater than about 4.0.

In another embodiment, Z is a moiety having a pK value between 4.5-7.0, more preferably between 5-6.5, and most preferably between 5-6.

In a preferred neutral cationic lipid, Z is an imidazole moiety, which has a pK of about 6.0. At physiologic pH of 7.4, this moiety is predominantly neutral, but at pH values of less than 6.0, the moiety becomes predominantly positive. A reaction scheme for preparation of the exemplary neutral cationic lipid is illustrated in FIG. 1 and details of the synthesis are provided in Example 10. Briefly, the para-nitrophenyl carbonate of 1,2-distearoyl glycerol (Compound III) was prepared from 1,2-distearoyl-sn-glycerol (Compound I) and para-nitrophenyl chloroformate (Compound II) and reacted with histamine (Compound IV) to yield a lipid (Compound V) having a imidazole moiety linked to a distearoyl tail via a carbamate linkage. A similar route, using glycerol in place of 1-amino-2,3-propanediol, can be used to produce a carbonate-linked product (L=—O—(C=O)—O—CH$_2$—). Further neutral cationic lipids suitable for use in the present invention are described in co-owned PCT Publication No. WO 01/26629.

The lipids of the invention can be prepared using standard synthetic methods. The lipids of the invention are further commercially available (Avanti Polar Lipids, Inc., Birmingham, Ala.).

B. Lipid-DTB-Polymer

The liposomes of the invention also include a lipid derivatized with a is hydrophilic polymer via a releasable bond, such as a dithiobenzyl moiety. This lipid-polymer component has the general structure:

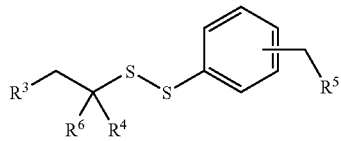

wherein $R^3$ comprises a hydrophilic polymer including a functional group suitable for covalently attaching the polymer to the dithiobenzyl moiety. $R^4$ and $R^6$ are independently selected to be H, an alkyl or an aryl, and can be varied to tailor the rate of disulfide cleavage. For example, to achieve a faster rate of cleavage, $R^4$ and $R^6$ are hydrogen. A slower rate of cleavage is achieved by sterically hindering the disulfide by selecting an alkyl or aryl for one or both of $R^4$ and $R^6$. $R^5$ comprises a linking moiety joined to $R^7$, which comprises an amine-containing lipid. The linking moiety in preferred embodiments is O(C=O), S(C=O) or O(C=O). The amine-containing lipid $R^7$ can be a primary or a secondary amine and can be selected from any number of lipids, including those described below. The orientation of the group CH$_2$—$R^5$ can be either ortho or para.

The amine-containing lipid $R^7$ is typically a water-insoluble molecule having at least one acyl chain containing at least about eight carbon atoms, more preferably an acyl chain containing between about 8-24 carbon atoms. A preferred lipid is a lipid having an amine-containing polar head group and an acyl chain. Exemplary lipids are phospholipids having a single acyl chain, such as stearoylamine, or two acyl chains. Preferred phospholipids with an amine-containing head group include phosphatidylethanolamine and phosphatidylserine. The lipid tail(s) can have between about 12 to about 24 carbon atoms and can be fully saturated or unsaturated. One preferred lipid is distearoylphosphatidylethanolamine (DSPE); however those of skill in the art will appreciate the wide variety of lipids that fall within this description. It will also be appreciated that the lipid can naturally include an amine group or can be derivatized to include an amine group. Other lipid moieties that do not have an acyl tail, such as cholesterolamine, are also suitable.

Figure 2:
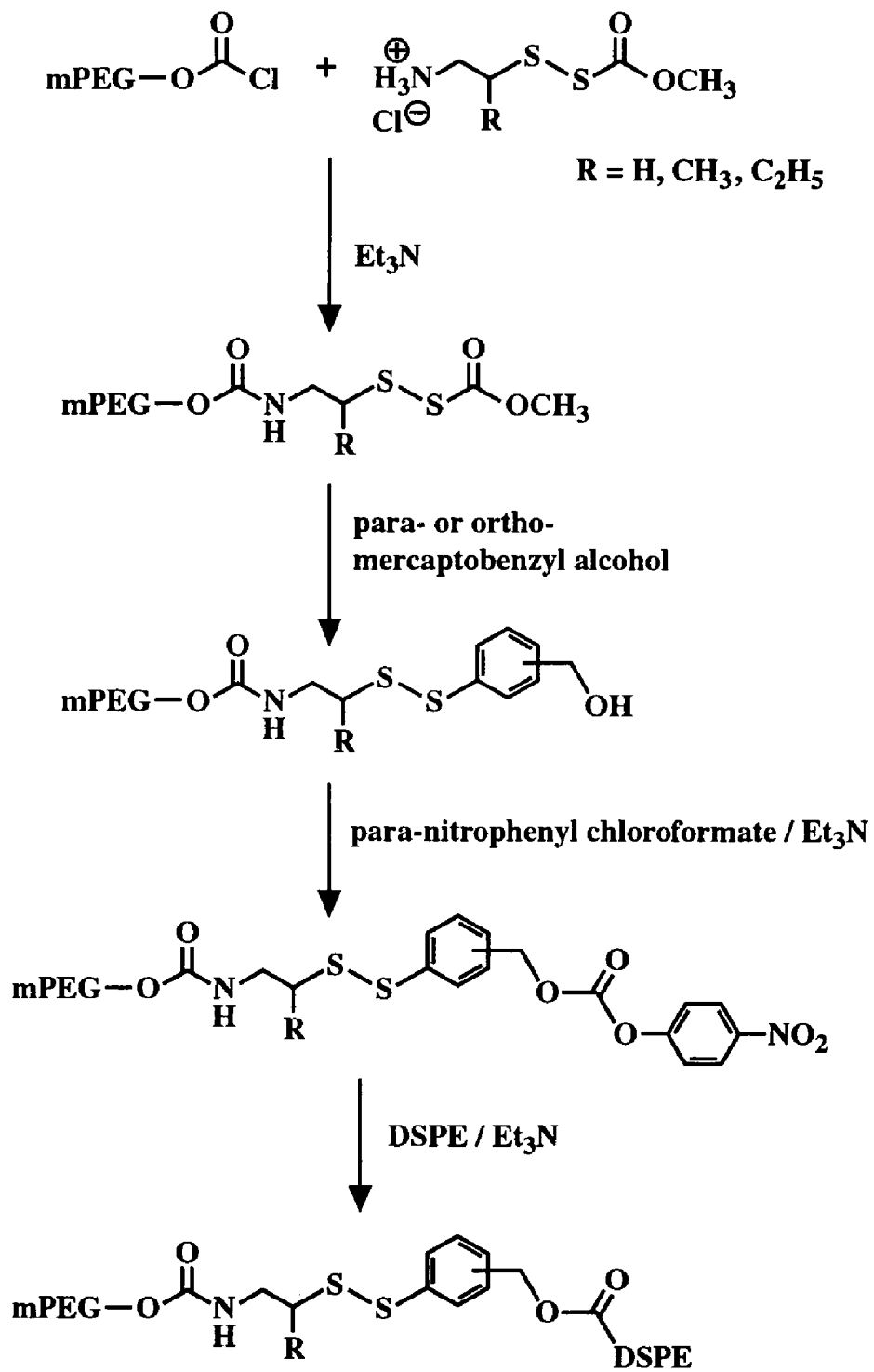
FIG. 2 illustrates a synthetic reaction scheme for synthesis of the mPEG-DTB-amine-lipid, where the amine-ligand is the lipid distearoylphosphatidylethanolamine (DSPE)

Synthesis of a polymer-DTB-lipid compound is schematically depicted in FIG. 2. mPEG derivatives (MW 2000 and 5000 Daltons) having a methoxycarbonyldithioalkyl end group were prepared by reacting 2-(methoxycarbonyldithio) ethaneamine with mPEG-chloroformate, which was readily prepared by phosgenation of dried mPEG-OH solution (Zalipsky, S., et al., *Biotechnol. Appl. Biochem.* 15:100-114 (1992).). The former compound was obtained through 2-aminoethanethiol hydrochloride reaction with an equivalent amount of methoxycarbonylsulfenyl chloride, according to published procedures (Brois, S. J., et al., *J. Amer. Chem. Soc.* 92:7629-7631 (1970); Koneko, T., et al., *Bioconjugate Chem.* 2:133-141 (1991)). Both the para and ortho isomers of mercaptobenzyl alcohol (Grice, R., et al., *J. Chem. Soc.* 1947-1954 (1963)) coupled cleanly with the resulting PEG-linked acyldisulfide, yielding mPEG bearing a dithio benzyl alcohol end group. Active carbonate introduction proceeded as with underivatized mPEG-OH, to give the para-nitrophenyl carbonate. Addition of DSPE in ethanolamine formed the desired mPEG-DTB-DSPE product. Both ortho- and para-DTB-lipid compounds were prepared and purified by silica gel chromatography and characterized by NMR and MALDI-TOFMS, the details of which are given in Example 1.

Figure 3:
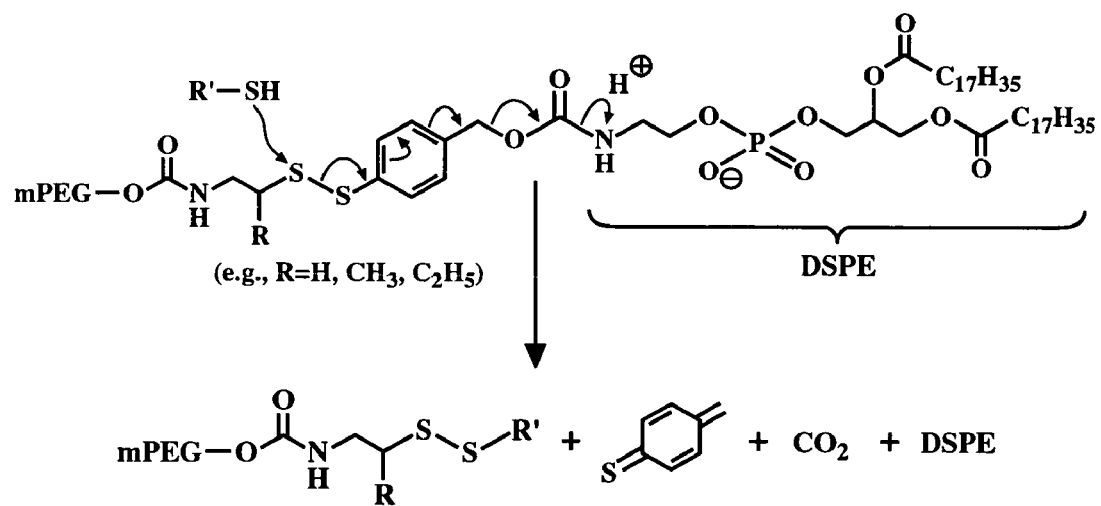
FIG. 3 illustrates the thiolytic cleavage mechanism of a para-dithiobenzyl urethane (DTB)-linked mPEG-DSPE conjugate.

FIG. 3 shows the mechanism of thiolytic cleavage of the mPEG-DTB-DSPE conjugate. Upon cleavage, the phosphatidylethanolamine lipid is regenerated in its natural, unmodified form.

Figure 4A:
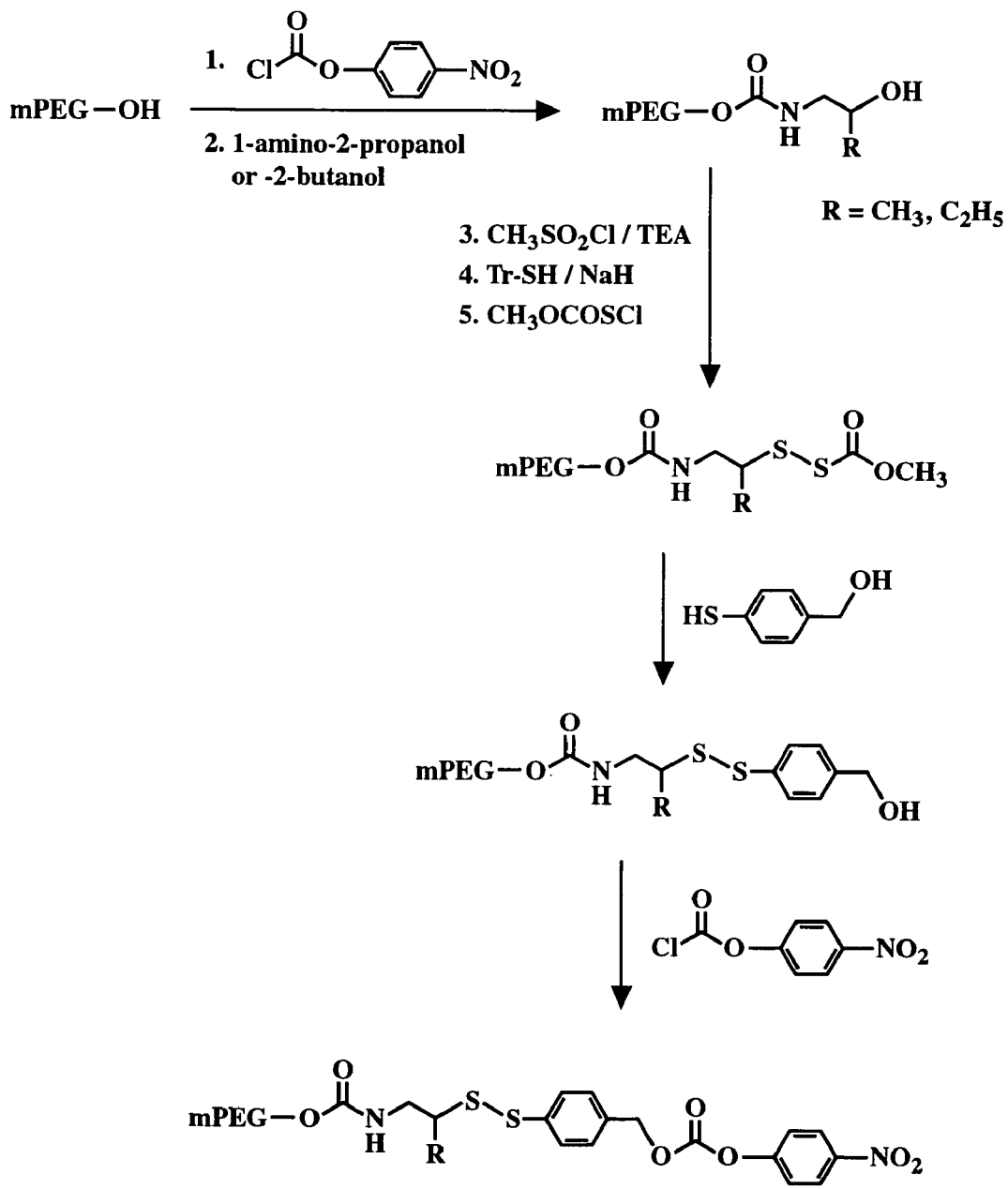
FIGS. 4A-4B show a synthetic reaction scheme for preparation of an mPEG-DTB-DSPE compound in accord with the invention where the DTB linkage is sterically hindered by an alkyl group.
Figure 4B:
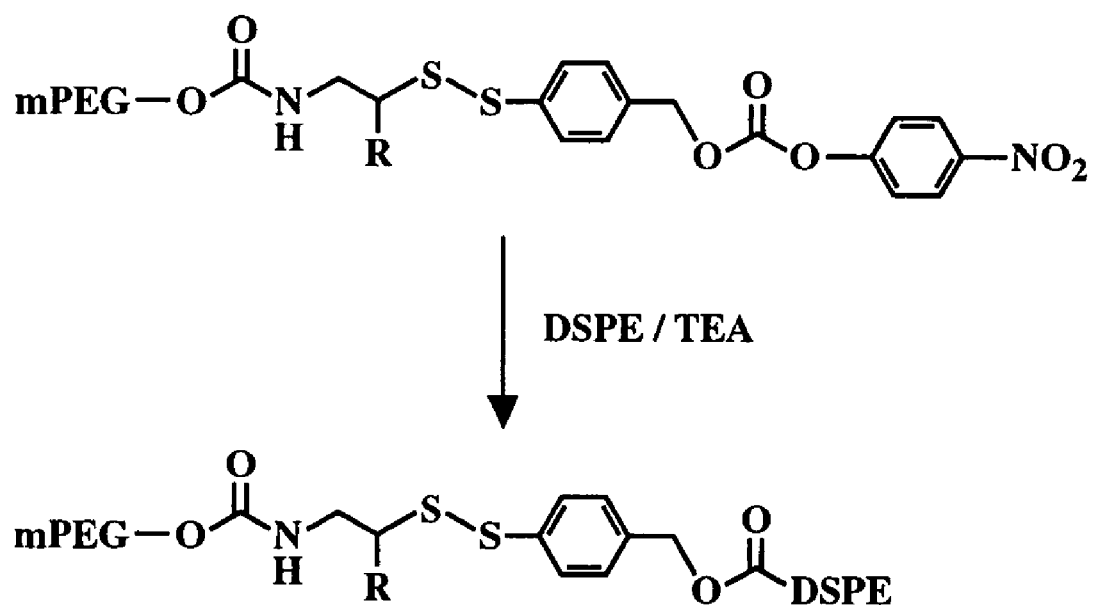

FIGS. 4A-4B show a reaction scheme for synthesis of mPEG-DTB-DSPE conjugates having an alkyl group adjacent the disulfide linkage, e.g., a more hindered disulfide linkage. As described more fully in Example 2A, mPEG-OH in dichloromethane was reacted with p-nitrophenylchloroformate in the presence of triethylamine (TEA) to form mPEG-nitrophenyl carbonate. An amino alcohol, such as 1-amino-2-propanol or 1-amino-2-butanol, in dimethylformamide (DMF) was reacted with the mPEG-nitrophenyl carbonate in the presence of TEA to form a secondary alcohol attached to PEG. The secondary alcohol was then converted to the desired mPEG-DTB-DSPE compound as illustrated in FIG. 4A and detailed in Example 2A.

In this reaction scheme, mPEG-methyl-dithiobenzyl-nitrophenyl chloroformate was reacted with DSPE to form the desired compound. The nitrophenyl chloroformate moiety in the mPEG-methyl-dithiobenzyl-nitrophenyl chloroformate compound acts as a leaving group to yield the desired product upon reaction with a selected lipid. The compound can also be produced by reaction with a compound such as mPEG-methyl-dithiobenzyl-$R^3$, where $R^3$ represents a leaving group joined through a linking moiety to the benzene ring. The leaving group is displaced upon reaction with an amine-containing ligand, such as DSPE, a polypeptide or an amine-containing drug. The leaving group is selected according to the reactivity of the amine in the ligand, and is preferably derived from various acidic alcohols that have a hydroxy- or oxy-containing leaving group. These include chloride, p-nitrophenol, o-nitrophenol, N-hydroxy-tetrahydrophthalimide, N-hydroxysuccinimide, N-hydroxy-glutarimide, N-hydroxynorbornene-2,3-dicarboxyimide, 1-hydroxybenzotriazole, 3-hydroxypyridine, 4-hydroxypyridine, 2-hydroxypyridine, 1-hydroxy-6-trifluoromethylbenzotriazole, imidazole, triazole, N-methyl-imidazole, pentafluorophenol, trifluorophenol and trichlorophenol.

Example 2B describes preparation of an mPEG-EtDTB-lipid conjugate where the disulfide linkage is hindered by an ethyl moiety.

Figure 5:
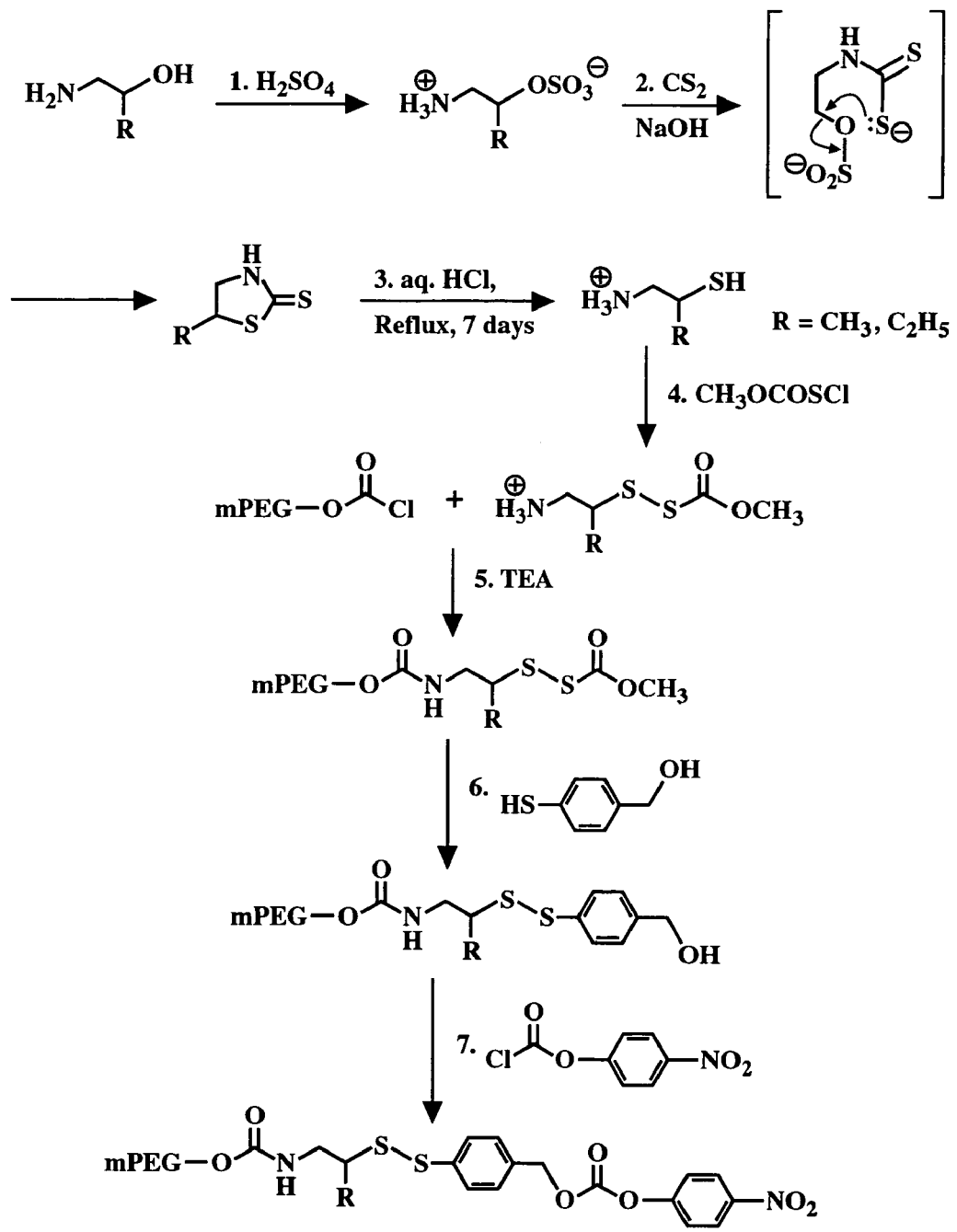
FIG. 5 shows another synthetic reaction scheme for preparation of an mPEG-DTB-ligand compound in accord with the invention.

FIG. 5 shows another synthetic reaction scheme for preparation of an mPEG-DTB-ligand compound in accord with the invention. The details of the reaction procedure are given in Examples 3A-3B. Briefly, cold 1-amino-2-propanol was reacted with sulfuric acid to form 2-amino-1-methylethyl hydrogen sulfate. This product was reacted with carbon disulfide and sodium hydroxide in aqueous ethanol to yield 5-methylthiazolidine-2-thione. An aqueous solution of hydrochloric acid was added to the 5-methylthiazolidine-2-thione and heated. After refluxing for one week, the product, 1-mercapto(methyl)ethyl ammonium chloride, was crystallized and recovered. This product was reacted with methoxy carbonylsulfenyl chloride to yield 2-(methoxycarbonyldithio)ethaneamine. Reaction of the 2-(methoxycarbonyldithio)ethaneamine with mPEG-chloroformate using the procedure described above with respect to FIG. 2 yields the desired mPEG-DTB-nitrophenyl compound suitable for reaction with a selected amine-containing lipid.

Example 3B describes the reaction for synthesis of mPEG-(ethyl)DTB-nitrophenyl.

Figure 6A:
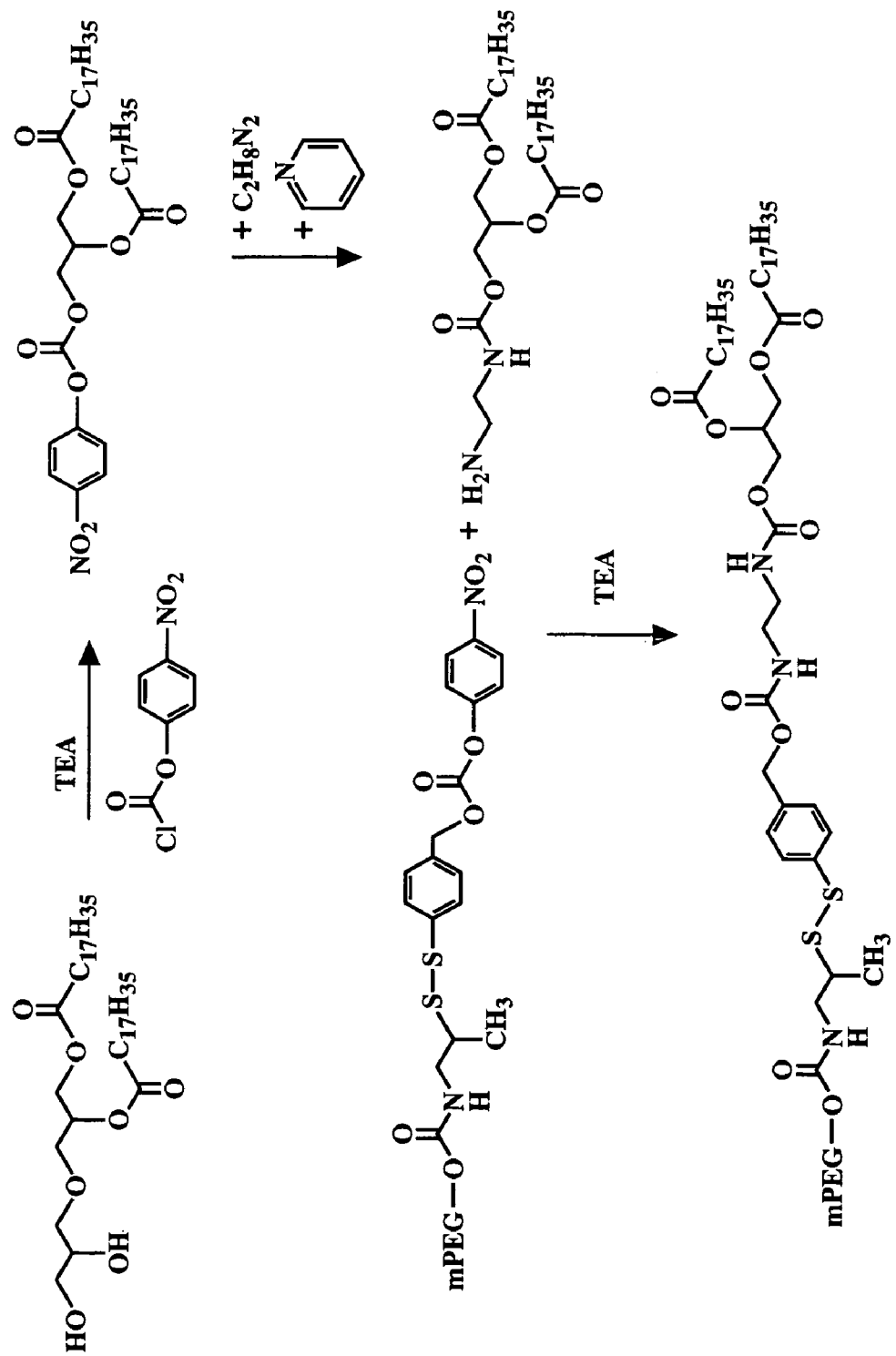
FIG. 6A is a synthetic reaction scheme for synthesis of an mPEG-DTB-lipid which upon thiolytic cleavage yields a cationic lipid.
Figure 6B:
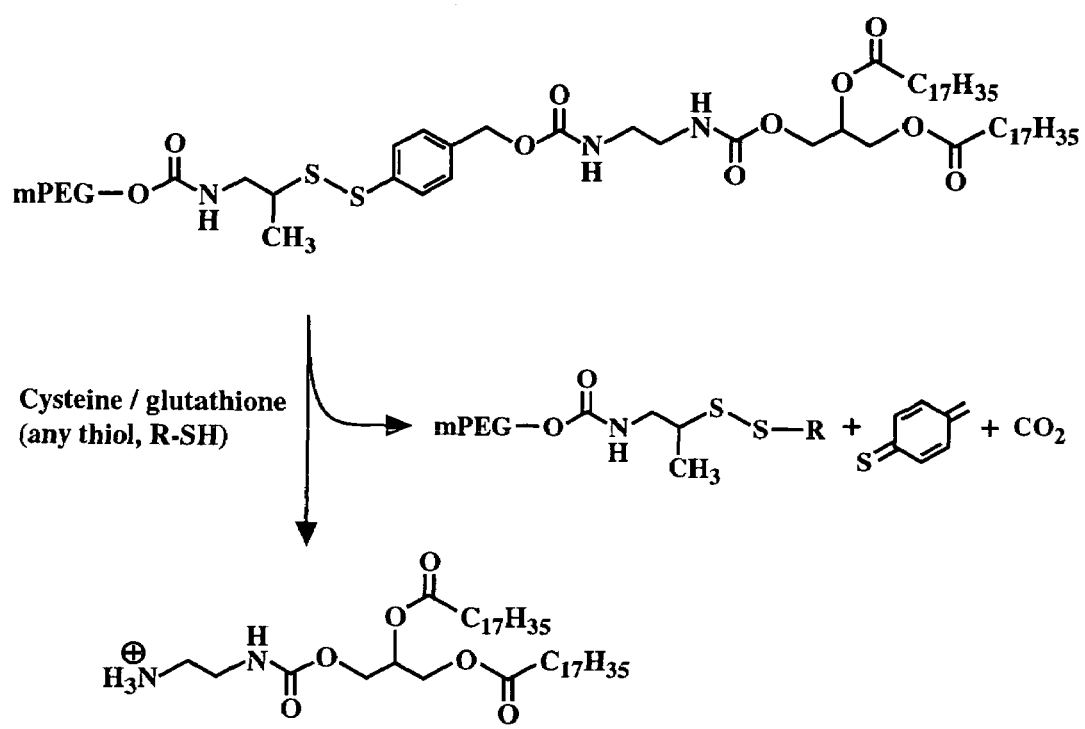
FIG. 6B shows the products after thiolytic cleavage of the compound in FIG. 6A.

FIG. 6A shows a reaction scheme for preparation of another mPEG-DTB-lipid compound in accord with the invention. The reaction details are provided in Example 4. The lipid 1,2-distearoyl-sn-glycerol is activated for reaction with mPEG-DTB-nitropheynl, prepared as described in FIG. 4A or FIG. 5. The resulting mPEG-DTB-lipid differs from the compounds described above in the absence of a phosphate head group. The mPEG-DTB-lipid of FIG. 6A is neutral prior to cleavage. As shown in FIG. 6B, upon thiolytic reduction of the disulfide bond, the compound decomposes to yield a cationic lipid. The positively-charged lipid provides for electrostatic interaction in vivo and commensurate advantages in in vivo targeting. Cleavage of the disulfide bond may be achieved by administration of a reducing agent, spontaneously before the liposome is internalized in the cell, or by reducing agents or conditions in vivo.

In the reaction schemes described above, $R^6$ of the claimed compound is H. However, in other embodiments $R^6$ is an alkyl or an aryl moiety. In this approach, for example where $R^4$ and $R^6$ are both $CH_3$ moieties, an α,β-unsaturated acyl chloride (R'RR"C=CHCOCl, where R' is, for example $CH_3$ and R" is $CH_3$, however any alkyl or aryl is contemplated) is reacted with an amine-terminated PEG to give the corresponding N-PEG-substituted α,β-unsaturated amide. This compound is reacted with thiolacetic acid, giving the corresponding N-PEG-substituted β-(acetylthio)amide via conjugate addition to the C=C bond. The acetylthio group (—SCOCH$_3$) is hydrolyzed to a thiol group (—SH), which is then reacted with methyl (chlorosulfenyl)formate (ClSCOOCH$_3$), generating a methoxycarbonyl dithio group (—SSCOOCH$_3$); this intermediate is then reacted with p-mercapto benzyl alcohol to give the N-PEG-substituted β-(dithiobenzyl alcohol)amide (having the structure PEG-NH—CO—CH$_2$CR'R"—SS-p-phenyl-CH$_2$OH). The benzyl alcohol moiety is then reacted with nitrophenyl chloroformate to give the nitrophenyl carbonate leaving group, as above.

As will be described below, liposomes comprised of the cationic lipid and the polymer-DTB-lipid were prepared in studies in support of the invention.

C. Nucleic Acid

In a preferred embodiment of the invention, the liposomes formed of the lipids described above are associated with a nucleic acid. By "associated" it is meant that a therapeutic agent, such as a nucleic acid, is entrapped in the liposomes central compartment and/or lipid bilayer spaces, is associated with the external liposome surface, or is both entrapped internally and externally associated with the liposomes. It will be appreciated that the therapeutic agent can be a nucleic acid or a drug compound. It will also be appreciated that a drug compound can be entrapped in the liposomes and a nucleic acid externally associated with the liposomes, or vice versa. The liposomes may be associated with the nucleic acid by any method known in the art. An exemplary method is detailed in Example 5.

In a preferred embodiment of the invention, a nucleic acid is associated with the liposomes. The nucleic acid can be selected from a variety of DNA and RNA based nucleic acids, including fragments and analogues of these. A variety of genes for treatment of various conditions have been described, and coding sequences for specific genes of interest can be retrieved from DNA sequence databanks, such as GenBank or EMBL. For example, polynucleotides for treatment of viral, malignant and inflammatory diseases and conditions, such as, cystic fibrosis, adenosine deaminase deficiency and AIDS, have been described. Treatment of cancers by administration of tumor suppressor genes, such as APC, DPC4, NF-1, NF-2, MTS1, RB, p53, WT1, BRCA1, BRCA2 and VHL, are contemplated.

Examples of specific nucleic acids for treatment of an indicated conditions include: HLA-B7: tumors, colorectal carcinoma, melanoma; IL-2: cancers, especially breast cancer, lung cancer, and tumors; IL-4: cancer; TNF: cancer; IGF-1 antisense: brain tumors; IFN: neuroblastoma; GM-CSF: renal cell carcinoma; MDR-1: cancer, especially advanced cancer, breast and ovarian cancers; and HSV thymidine kinase: brain tumors, head and neck tumors, mesothelioma, ovarian cancer.

The polynucleotide can be an antisense DNA oligonucleotide composed of sequences complementary to its target, usually a messenger RNA (mRNA) or an mRNA precursor. The mRNA contains genetic information in the functional, or sense, orientation and binding of the antisense oligonucleotide inactivates the intended mRNA and prevents its translation into protein. Such antisense molecules are determined based on biochemical experiments showing that proteins are translated from specific RNAs and once the sequence of the RNA is known, an antisense molecule that will bind to it through complementary Watson-Crick base pairs can be designed. Such antisense molecules typically contain between 10-30 base pairs, more preferably between 10-25, and most preferably between 15-20.

The antisense oligonucleotide can be modified for improved resistance to nuclease hydrolysis, and such analogues include phosphorothioate, methylphosphonate, phosphodiester and p-ethoxy oligonucleotides (WO 97/07784).

The entrapped agent can also be a ribozyme, DNAzyme, or catalytic RNA.

The nucleic acid or gene can, in another embodiment, be inserted into a plasmid, preferably one that is a circularized or closed double-stranded molecule having sizes preferably in the 5-40 Kbp (kilo basepair) range. Such plasmids are constructed according to well-known methods and include a therapeutic gene, i.e., the gene to be expressed in gene therapy, under the control of suitable promoter and enhancer, and other elements necessary for replication within the host cell and/or integration into the host-cell genome. Methods for preparing plasmids useful for gene therapy are widely known and referenced.

In another embodiment, the nucleic acid or gene can be used for gene therapy for long term, stable therapy. Thus, DNA isolates as well as DNA expression vehicles containing gene sequences encoding a gene are considered. In one embodiment, an expression vehicle coding for human Factor VIII is entrapped in the liposome. Suitable vectors specific for Factor VIII and Factor VIII sequences are described in the art, for example, in U.S. Pat. No. 5,668,108. Factor VIII is a protein normally present in plasma, and a decreased level or absence of the protein is the cause of hemophilia A. Hemophilia is an inherited disease now known to be present in different forms: hemophilia A, hemophilia B, and hemophilia C. Hemophilia A is the most frequent form with a clinical manifestation of a strong bleeding tendency. This is due to a lack of sufficient fibrin formation required for platelet plug stabilization, resulting in a plug which is easily dislodged with subsequent rebleeding at the injury site.

Polynucleotides, oligonucleotides, other nucleic acids, such as a DNA plasmid, can be entrapped in the liposome by passive entrapment during hydration of the lipid film. Other procedures for entrapping polynucleotides include condensing the nucleic acid in single-molecule form, where the nucleic acid is suspended in an aqueous medium containing protamine sulfate, spermine, spermidine, histone, lysine, mixtures thereof, or other suitable polycationic condensing agent, under conditions effective to condense the nucleic acid into small particles. The solution of condensed nucleic acid molecules is used to rehydrate a dried lipid film to form liposomes with the condensed nucleic acid in entrapped form.

D. Targeting Ligand

The liposomes may optionally be prepared to contain surface groups, such as antibodies or antibody fragments, small effector molecules for interacting with cell-surface receptors, antigens, and other like compounds, for achieving desired target-binding properties to specific cell populations. Such ligands can be included in the liposomes by including in the liposomal lipids a lipid derivatized with the targeting molecule, or a lipid having a polar-head chemical group that can be derivatized with the targeting molecule in preformed liposomes. Alternatively, a targeting moiety can be inserted into preformed liposomes by incubating the preformed liposomes with a ligand-polymer-lipid conjugate.

Lipids can be derivatized with the targeting ligand by covalently attaching is the ligand to the free distal end of a hydrophilic polymer chain, which is attached at its proximal end to a vesicle-forming lipid. There are a wide variety of techniques for attaching a selected hydrophilic polymer to a selected lipid and activating the free, unattached end of the polymer for reaction with a selected ligand, and in particular, the hydrophilic polymer polyethyleneglycol (PEG) has been widely studied (Allen, T. M., et al., *Biochemicia et Biophysica Acta* 1237:99-108 (1995); Zalipsky, S., *Bioconjugate Chem.*, 4(4):296-299 (1993); Zalipsky, S., et al., *FEBS Lett.* 353:71-74 (1994); Zalipsky, S., et al., *Bioconjugate Chemistry*, 705-708 (1995); Zalipsky, S., in *STEALTH LIPOSOMES* (D. Lasic and F. Martin, Eds.) Chapter 9, CRC Press, Boca Raton, Fla. (1995)).

Targeting ligands are well known to those of skill in the art, and in a preferred embodiment of the present invention, the ligand is one that has binding affinity to endothelial tumor cells, and which is, more preferably, internalized by the cells. Such ligands often bind to an extracellular domain of a growth factor receptor. Exemplary receptors include the c-erbB-2 protein product of the HER2/neu oncogene, epidermal growth factor (EGF) receptor, basic fibroblast growth receptor (basic FGF) receptor and vascular endothelial growth factor receptor, E-, L- and P-selectin receptors, folate receptor, CD4 receptor, CD19 receptor, αβ integrin receptors and chemokine receptors. Further ligands are described in co-owned U.S. Pat. No. 6,043,094, incorporated by reference herein.

Further, targeting ligands can be paired with specific nucleic acids for treatment of indicated conditions. For example, where the nucleic acid is an expression vector encoding for Factor VIII, a preferred ligand is one that has binding affinity to hepatocytes and/or which initiates internalization of the liposomes by the cells. A preferred targeting ligand for use with an expression vector coding for Factor VIII is galactose.

III. Preparation of the Composition

A. Liposome Component

Liposomes containing the lipids described above, that is, the cationic lipid and the polymer-DTB-lipid, can be prepared by a variety of techniques, such as those detailed in Szoka, F., Jr., et al., *Ann. Rev. Biophys. Bioeng.* 9:467 (1980), and specific examples of liposomes prepared in support of the present invention will be described below. Typically, the liposomes are multilamellar vesicles (MLVs), which can be formed by simple lipid-film hydration techniques. In this procedure, a mixture of liposome-forming lipids of the type detailed below is dissolved in a suitable organic solvent which is then evaporated in a vessel to form a thin film. The lipid film is then covered by an aqueous medium, hydrating to form MLVs, typically with sizes between about 0.1 to 10 microns.

Liposomes for use in the composition of the invention include (i) the cationic lipid and (ii) a lipid covalently attached to a hydrophilic polymer through a DTB linkage. The liposomes can also include other components, such as vesicle-forming lipids or a lipid that is stably incorporated into the liposome lipid bilayer, such as diacylglycerols, lysophospholipids, fatty acids, glycolipids, cerebrosides and sterols, such as cholesterol.

Typically, liposomes are comprised of between about 10-90 mole percent of the cationic lipid, more preferably between about 20-80 mole percent, and still more preferably between about 30-70 mole percent. The polymer-DTB-lipid is typically included in a molar percentage of between about 1-20, more preferably between about 2-15 mole percent, and still more preferably between about 4-12 mole percent. In studies performed in support of the invention, described below, liposomes comprised of about 50 to 55 mole percent cationic lipid and 0.5-5 mole percent of polymer-DTB-lipid.

Liposomes prepared in accordance with the invention can be sized to have substantially homogeneous sizes in a selected size range, typically between about 0.01 to 0.5 microns, more preferably between 0.03-0.40 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in *SPECIALIZED DRUG DELIVERY SYSTEMS-MANUFACTURING AND PRODUCTION TECHNOLOGY*, (P. Tyle, Ed.) Marcel Dekker, New York, pp. 267-316 (1990)).

B. Preparation and Characterization of Exemplary Compositions

In studies performed in support of the invention, a PNSL luciferase plasmic DNA with a CMV promoter was entrapped in liposomes comprised of the cationic lipid and the polymer-DTB-lipid as detailed in Example 5. Targeted liposome complexes were achieved by including folate as a targeting ligand. Typically, the targeting ligand is covalently attached to the distal end of the PEG-DSPE. Attachment of targeting ligands is known in the art and described, for example, in U.S. Pat. No. 6,180,134.

Example 6 describes preparation of Formulation Nos. 1-20 for in vitro incubation with BHK cells to determine transfection efficiency with luciferase. All formulations were prepared using cationic liposomes composed of dioleoyl-trimethylamminium-propane (DOTAP) and cholesterol (CHOL) in a molar ratio of 55:45. Formulation Nos. 1, 3, and 5 included non-cleavable mPEG-DSPE at a molar ratio of 0.5, 2.0, and 5.0% of the total lipids, respectively. Formulations 2, 4, and 6 were similar to 1, 3, and 5 with the addition of a folate targeting ligand. Formulations 7-18 used cleavable PEG-Me-DTB-DSPE and PEG-H-DTB-DSPE, at similiar concentrations, with and without a folate targeting ligand. Formulation Nos. 19 and 20 served as comparative controls.

The liposome-DNA complexes were incubated with the cell cultures for 2 hours. Twenty four hours later, the cells were harvested and assayed for luciferase transfection. The results are shown in Table 1.

TABLE 1

Luciferase Transfection Efficiency After Incubation with BHK Cell Culture

| Formulation No. (See Example 6 for details) | Sample 20 µg/well | | Average RLU/20 µl | Luciferase (pg luciferase/mg protein) |
|---|---|---|---|---|
| 1 | 5777 | 6056 | 5916.5 | 2993 |
| 2 | 4463 | 4531 | 4497 | 2251 |
| 3 | 1658 | 1734 | 1696 | 819 |
| 4 | 1436 | 1477 | 1456.5 | 699 |
| 5 | 1449 | 1533 | 1491 | 716 |
| 6 | 890 | 954 | 922 | 435 |
| 7 | 13683 | 14123 | 13903 | 7259 |
| 8 | 8018 | 8108 | 8063 | 4126 |
| 9 | 2598 | 2650 | 2624 | 1288 |
| 10 | 2921 | 2893 | 2907 | 1432 |
| 11 | 2147 | 2141 | 2144 | 1044 |
| 12 | 2110 | 2114 | 2112 | 1028 |
| 13 | 22615 | 22974 | 22794.5 | 12123 |
| 14 | 16070 | 16797 | 16433.5 | 8634 |
| 15 | 8012 | 8473 | 8242.5 | 4221 |
| 16 | 9606 | 10065 | 9835.5 | 5070 |
| 17 | 5965 | 6054 | 6009.5 | 3041 |
| 18 | 6106 | 6378 | 6242 | 3163 |
| 19 | 15512 | 16228 | 15870 | 8327 |
| 20 | 77586 | 80707 | 79146.5 | 44089 |

As seen from the results in Table 1, the gene expression lost due to the inclusion of mPEG-DSPE in the complexes was at least partially restored when the cleavable PEG-lipids were used. The extent of the transfection was inversely dependent not only on their formulation content, but also on the ease of the conjugate cleavability. Of the two DTB-linked lipopolymers, the more sterically hindered derivative (PEG-Me-DTB-DSPE) was considerably slower in cleaving. The luciferase transfection efficiency for the liposomes including 0.5% PEG-H-DTB-DSPE (Formulation No. 13) was greater than 2.5-fold higher than the corresponding non-cleavable PEG formulation (Formulation 1) and nearly 1.5-fold greater than the corresponding PEG-Me-DTB-DSPE formulation (Formulation 7). Formulations 13-18 all included the cleavable PEG-H-DTB-DSPE. These formulations showed a transfection efficiency of more than 2.5 to at least 8-fold greater than the non-cleavable PEG formulations (Formulations 1-6). The positive control expression level was completely restored at 0.5 mole % of mPEG-H-DTB-DSPE (Formulation 13), and was partially restored for mPEG-Me-DTB-DSPE (Formulation 7).

Example 7 describes in vitro incubation of a KbHiFr cell line with Formulation Nos. 1-20 as described in Example 6 to determine transfection efficiency with luciferase.

The liposome-DNA complexes were incubated with the cell cultures for 2 hours. Twenty four hours later, the cells were harvested and assayed for luciferase transfection and protein assay. The results are shown in Table 2.

TABLE 2

Luciferase Transfection Efficiency After Incubation with KbHiFr Cell Culture

| Formulation No. (See Example 6 for details) | Sample 10 µL/well | | Average | Protein (mg/ml) | Luciferase pg/ml | Luciferase pg/mg protein |
|---|---|---|---|---|---|---|
| 1 | 0.754 | 0.658 | 0.706 | 2.49 | 2993 | 1203 |
| 2 | 0.635 | 0.523 | 0.579 | 1.73 | 2251 | 1302 |
| 3 | 0.559 | 0.61 | 0.585 | 1.76 | 819 | 465 |
| 4 | 0.662 | 0.581 | 0.622 | 1.98 | 699 | 353 |
| 5 | 0.52 | 0.555 | 0.538 | 1.48 | 716 | 484 |
| 6 | 0.615 | 0.605 | 0.610 | 1.91 | 435 | 227 |
| 7 | 0.503 | 0.546 | 0.525 | 1.40 | 7259 | 5170 |
| 8 | 0.535 | 0.578 | 0.557 | 1.60 | 4126 | 2586 |
| 9 | 0.548 | 0.544 | 0.546 | 1.53 | 1288 | 840 |
| 10 | 0.587 | 0.572 | 0.580 | 1.73 | 1432 | 827 |
| 11 | 0.532 | 0.56 | 0.546 | 1.53 | 1044 | 681 |
| 12 | 0.558 | 0.538 | 0.548 | 1.54 | 1028 | 666 |
| 13 | 0.546 | 0.569 | 0.558 | 1.60 | 12123 | 7571 |
| 14 | 0.647 | 0.527 | 0.587 | 1.78 | 8634 | 4858 |
| 15 | 0.486 | 0.47 | 0.478 | 1.13 | 4221 | 3748 |
| 16 | 0.522 | 0.546 | 0.534 | 1.46 | 5070 | 3471 |
| 17 | 0.476 | 0.457 | 0.467 | 1.06 | 3041 | 2876 |
| 18 | 0.451 | 0.465 | 0.458 | 1.01 | 3163 | 3142 |
| 19 | 0.524 | 0.503 | 0.514 | 1.34 | 8327 | 6222 |
| 20 | 0.508 | 0.435 | 0.472 | 1.09 | 44089 | 40545 |

Figure 7:
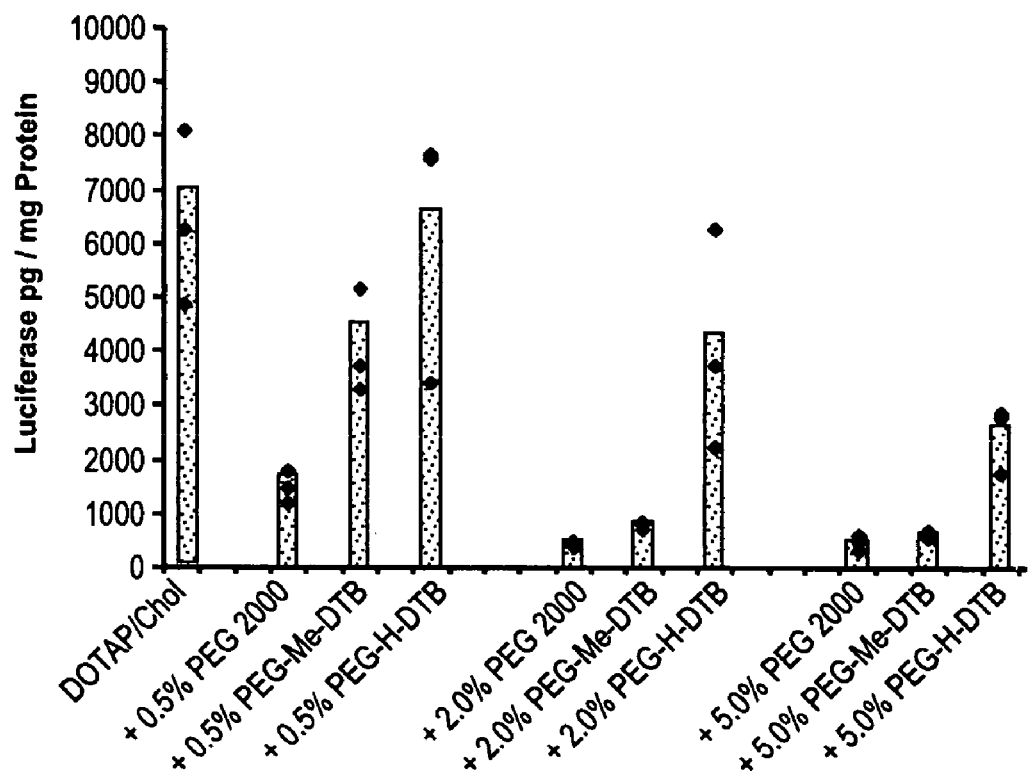
FIG. 7 shows luciferase expression, in pg/mg protein, for plasmid-liposome complexes prepared with various ratios of mPEG-DSPE and mPEG-DTB-DSPE.

As seen in FIG. 7, results regarding luciferase transfection were similar to those obtained in Example 6. The cleavable PEG formulations at least partially restored gene expression lost due to the inclusion of mPEG-DSPE in the complexes. For the liposomes including 0.5% of the cleavable lipopolymer, the PEG-H-DTB-DSPE (Formulation 13) completely restored the positive control expression level. The corresponding PEG-Me-DTB-DSPE formulation (Formulation 7) was more than 2.6-fold greater than the corresponding non-cleavable PEG formulation (Formulation 1).

As no cleaving agent was included in the incubation media, the data (shown in FIG. 7) suggests that the cleavable lipopolymers are degraded in the lysosomal compartment after charge-mediated cell binding and internalization. It can further be assumed that the cleavage of the PEG-lipids facilitates the liberation of DNA from the complexes and its release from the lysosome for the eventual expression of the DNA.

Figure 9:
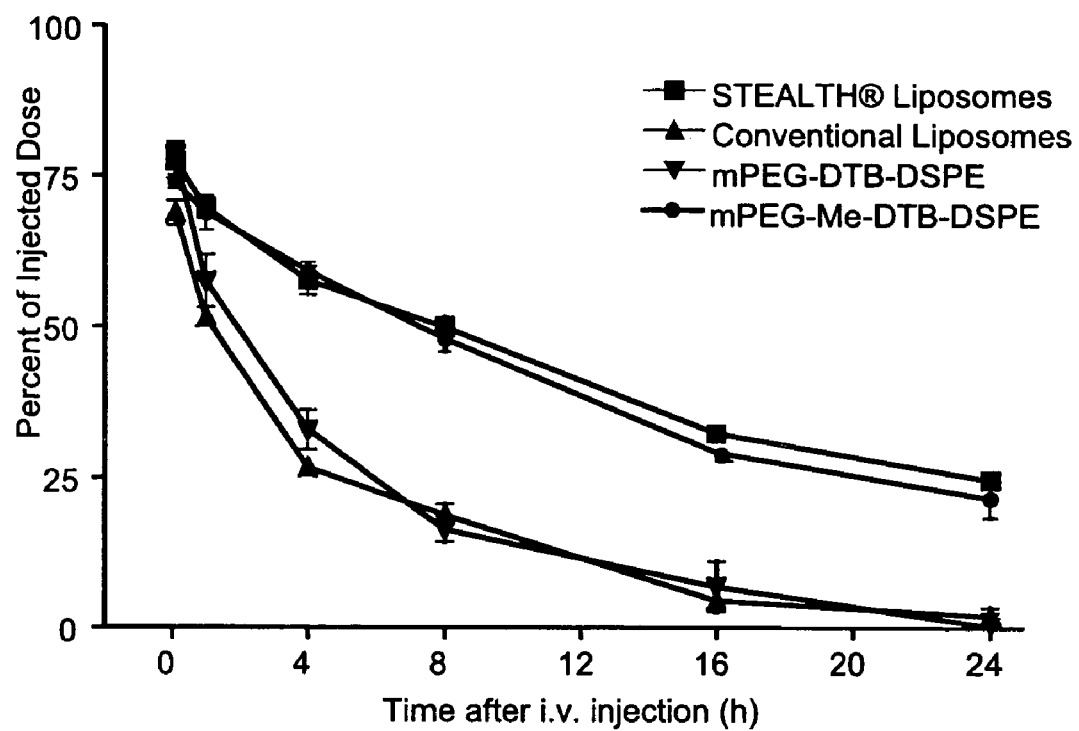
FIG. 9 shows in vivo plasma clearance of liposomes having mPEG-DTB-DSPE (▼), mPEG-Me-DTB-DSPE (●), mPEG-DSPE (STEALTH®, ■), and of liposomes having no PEG chains (conventional liposomes, ▲) 24 hours after injection.
Figure 10A:
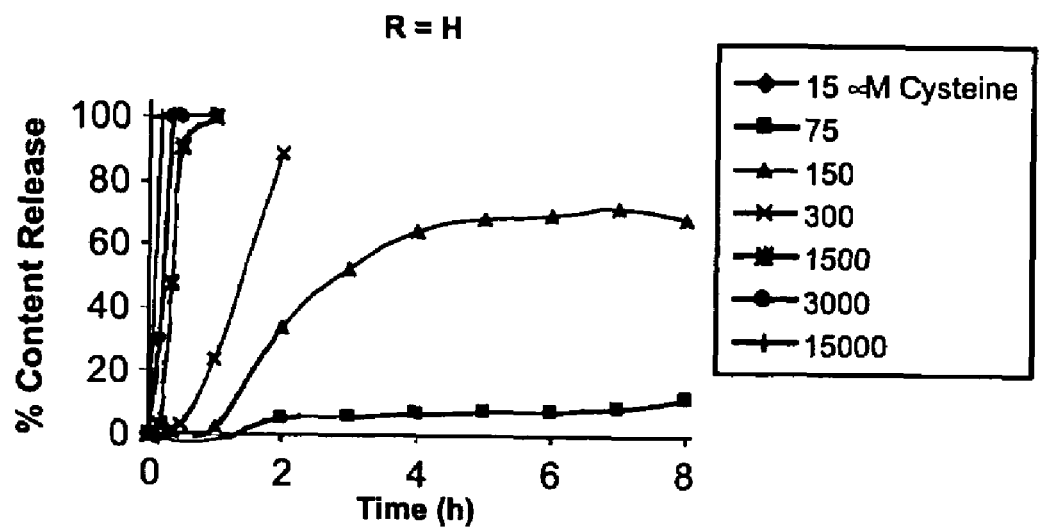
FIGS. 10A-10B show release of liposome entrapped fluorophores in response to cleavage by cysteine in liposomes prepared with mPEG-H-DTB-DSPE (FIG. 10A) and mPEG-Me-DTB-DSPE (FIG. 10B) at cysteine concentrations of 15 μM (◇), 75 μM (■), 150 μM (▲), 300 μM (x), 1500 μM (*), 3000 μM (●), and 15000 μM (|)
Figure 10B:
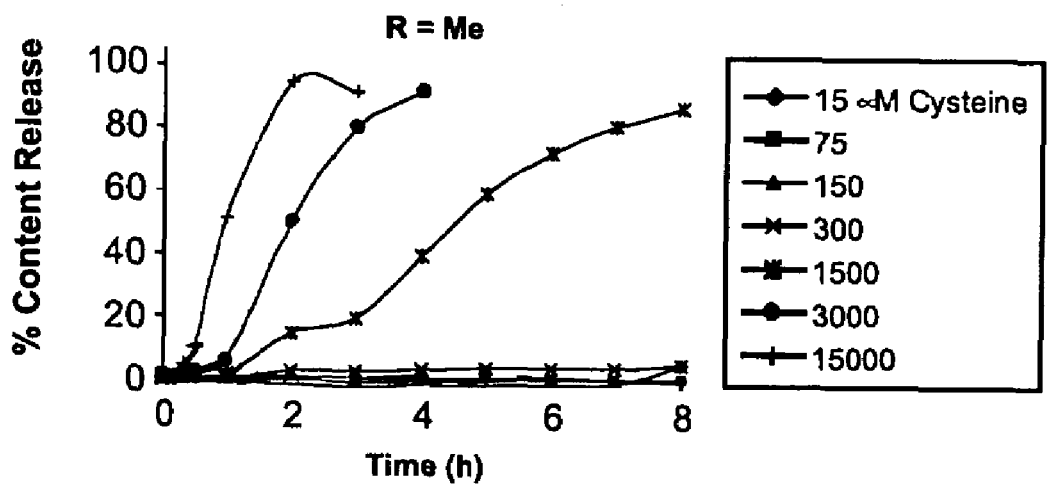

Example 8 describes in vitro incubation of a BHK cell line with a liposome-DNA complex to determine transfection efficiency in the presence of cysteine. The liposome-DNA complexes and cysteine were incubated with the cell cultures for 2 hours. Twenty four hours later, the cells were harvested and assayed for luciferase transfection and protein assay. The results are shown in Table 3.

seen in FIG. 10A, the more sterically hindered derivative (PEG-Me-DTB-DSPE) was considerably slower in cleaving than the PEG-H-DTB-DSPE derivative (FIG. 10B). As seen in FIGS. 10A-10B, the release rate was about 10-fold lower for the liposomes stabilized via the hindered disulfide. As shown in FIG. 9, further pharmacokinetic experiments in mice on $^{111}$In-labeled PHPC/Cholesterol/mPEG-DTB-DSPE liposomes revealed a STEALTH®-like profile with the PEG-Me-DTB-DSPE liposomes ($\approx$30% of the injected dose was still circulating after 24 hours). In contrast, liposomes including the faster-cleaving, PEG-H-DTB-DSPE, analog were cleared as rapidly as the PHPC/Cholesterol sample (about 1% of the injected dose available after 24 h). Accordingly, the Me-DTB conjugate is considerably more stable in the blood stream than the H-DTB conjugate.

Figure 11:
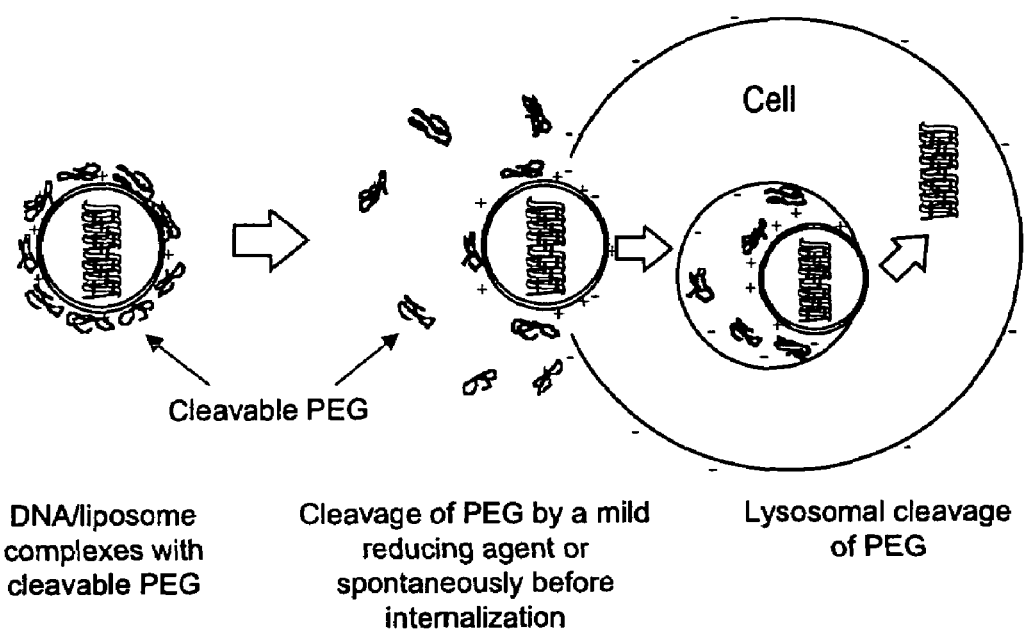
FIG. 11 illustrates intracellular delivery of DNA to a cell using a DNA/liposome complex.

FIG. 11 shows the steps of delivery of DNA from a DNA/liposome complex. It will be appreciated that the steps of delivery are applicable to any nucleic acid. First, the hydrophilic polymer, such as PEG, is cleaved by a reducing agent or spontaneously. This allows the positively charged liposome to interact with the negatively charged lipids of the cell membrane allowing internalization of the DNA/liposome complex and delivery of the DNA intracellularly.

TABLE 3

Luciferase Transfection Efficiency in the Presence of Cysteine

| Liposome Complex | Cysteine μM | Sample 10 μl/well | | Average | Protein (mg/ml) | Luciferase pg/ml | Luciferase pg/mg protein |
|---|---|---|---|---|---|---|---|
| mPEG2000-DSPE | 0 | 0.961 | 0.925 | 0.943 | 3.231 | 12248 | 3791 |
| | 50 | 0.997 | 1.171 | 1.084 | 4.051 | 20449 | 5048 |
| | 250 | 0.921 | 1.038 | 0.980 | 3.443 | 6009 | 1745 |
| | 1250 | 1.079 | 0.991 | 1.035 | 3.766 | 16322 | 4334 |
| mPEG-Me-DTB-DSPE | 0 | 1.08 | 0.898 | 0.989 | 3.498 | 731966 | 209240 |
| | 50 | 1.164 | 1.134 | 1.149 | 4.429 | 1274714 | 287791 |
| | 250 | 0.97 | 0.987 | 1.080 | 4.028 | 1659219 | 411945 |
| | 1250 | 0.948 | 0.956 | 0.952 | 3.283 | 2407217 | 733259 |
| mPEG-H-DTB-DSPE | 0 | 0.937 | 0.871 | 0.904 | 3.004 | 1780953 | 592945 |
| | 50 | 0.956 | 0.971 | 0.964 | 3.350 | 2503029 | 747213 |
| | 250 | 0.41 | 0.884 | 1.004 | 3.586 | 1833608 | 511395 |
| | 1250 | 1.031 | 0.866 | 0.949 | 3.263 | 1797497 | 550951 |
| Dotap/Chol | 0 | 1.017 | 1.106 | 1.062 | 3.920 | 2963052 | 755859 |
| | 50 | 1.039 | 1.149 | 1.094 | 4.109 | 3072417 | 747685 |
| | 250 | 0.393 | 0.415 | 0.404 | 1.879 | 2865832 | 1525588 |
| | 1250 | 1.068 | 1.121 | 1.095 | 4.112 | 1515346 | 368505 |
| lipofectamine/DNA | n/a | 0.778 | 0.768 | 0.773 | 2.241 | 1322871 | 590239 |

Figure 8:
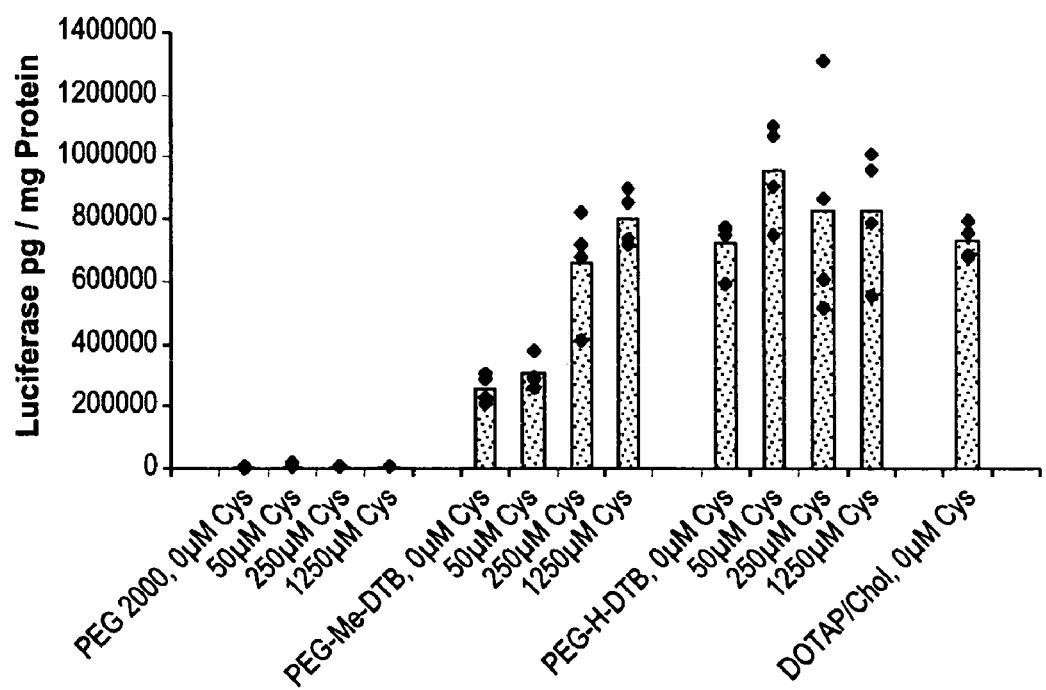
FIG. 8 shows luciferase expression, in pg/mg protein, for in vitro ransfection of liposome-DNA complexes prepared with mPEG-DSPE and mPEG-DTB-DSPE in various concentrations of cysteine.

The data shows a significant inhibition of gene expression when DNA-complexed liposomes were stabilized with mPEG-DSPE. As evidenced by the significant increase in luciferase transfection, the data shows that under thiolytic conditions (addition of cysteine), the cleavable lipopolymers were considerably cleaved. As mPEG-DSPE is resistant to thiolysis, the addition of cysteine did not affect the expression level as compared to Experiment 6. In contrast, utilization of the cleavable lipopolymers, allowed restoration of the initially-lost transfection efficiency by treatment with cysteine. Since the Me-DTB linker is more stable than H-DTB, under the same thiolytic conditions, this expression recovery was less pronounced for the complexes stabilized with the more hindered mPEG-Me-DTB-DSPE than with mPEG-H-DTB-DSPE (FIG. 8).

Example 9 describes a fluorophore-releasing assay performed on DOPE-liposomes in the presence of cysteine, a mild reagent present in physiological milieu. The liposomes included a DTB-linked lipopolymers, where R=H or Me. As

VI. EXAMPLES

The following examples illustrate but in no way are intended to limit the invention.

Materials: The following materials were obtained from the indicated source: partially hydrogenated soy phosphatidylcholine (Vernon Walden Inc., Green Village, N.J.); cholesterol (Sigma, St. Louis, Mo.); distearoyl phosphatidyl ethanolamine (DSPE), dioleoylphosphatidyl ethanolamine (DOPE), dimethyldioctadecylammonium (DDAB), and dioleoyltrimethylammonium-propane (DOTAP) (Avanti Polar Lipids, Inc., Birmingham, Ala.).

Example 1

Synthesis of mPEG-DTB-DSPE

The reaction scheme is illustrated in FIG. 2.

mPEG-MeDTB-nitrophenylcarbonate (300 mg, 0.12 mmol, 1.29 eq) was dissolved in CHCl$_3$ (3 ml). DSPE (70 mg, 0.093 mol) and TEA (58.5 μl, 0.42 mmol, 4.5 eq) were added to PEG-solution, and was stirred at 50° C. (oil bath temp). After 15 minutes, TLC showed that the reaction didn't go to completion. Then two portions of TEA (10 μl, and 20 μl), and few portions of mPEG-MeDTB-nitrophenylcarbonate (50 mg, 30 mg, 10 mg) were added every after 10 minutes, until the reaction went to completion. Solvent was evaporated. Product mixture was dissolved in MeOH, and 1 g of C8 silica was added. Solvent was evaporated again. Product containing C8 silica was added on the top of the column, and was eluted with MeOH:H$_2$O gradient (pressure), MeOH:H$_2$O=30:70, 60 ml; MeOH:H$_2$O=50:50, 60 ml; MeOH:H$_2$O=70:30, 140 ml (starting material eluted); MeOH:H$_2$O=75:25=40 ml; MeOH:H$_2$O=80:20, 80 ml (product eluted); MeOH:H$_2$O=85:15, 40 ml; MeOH:H$_2$O=90:10, 40 ml; MeOH=40 ml;CHCl$_3$:MeOH:H$_2$O=90:18:10, 40 ml. Fractions containing pure product were combined and evaporated to give product as colorless thick liquid. Tertiary butanol (5 ml) was added to it, lyophilized and the dried in vacuo over P$_2$O$_5$ to give product as white fluffy solid (252 mg, 89% yield).

The ortho- and para-DTB-DSPE compounds were purified by silica gel chromatography (methanol gradient 0-10% in chloroform, ≈70% isolated yield) and the structures confirmed by NMR and MALDI-TOFMS. ($^1$H NMR for para conjugate: (d6-DMSO, 360 MHz) δ 0.86 (t, CH$_3$, 6 H), 1.22 (s, CH$_2$ of lipid, 56H), 1.57 (m, CH$_2$CH$_2$CO$_2$, 4H), 2.50 (2×t, CH$_2$CO$_2$, 4H), 2.82 (t, CH$_2$S, 2H), 3.32 (s, OCH$_3$, 3H), 3.51 (m, PEG, ≈180 H), 4.07 (t, PEG-CH$_2$OCONH, 2H), 4.11 & 4.28 (2×dd CH$_2$CH of glycerol, 2H), 4.98 (s, benzyl-CH$_2$, 2H), 5.09 (m, CHCH$_2$ of lipid), 7.35 & 7.53 (2×d, aromatic, 4H) ppm. The ortho conjugate differed only in benzyl and aromatic signals at 5.11 (s, CH$_2$, 2H), and 7.31 (d, 1H), 7.39 (m, 2H) 7.75(d, 1H) ppm.

MALDI-TOFMS produced a distribution of ions spaced at equal 44 Da intervals, corresponding to the ethylene oxide repeating units. The average molecular weight of the compounds was 3127 and 3139 Da for para and ortho isomers respectively (theoretical molecular weight ≈3100 Da).

Example 2

Synthesis of mPEG-DTB-DSPE

A. mPEG-MeDTB-DSPE

This reaction scheme is illustrated in FIGS. 4A-4B.

mPEG(5K)-OH (40 g, 8 mmol) was dried azeotropically with toluene (total volume was 270 ml, 250 ml was distilled off by Dean-Stark). Dichloromethane (100 ml) was added to mPEG-OH. P-nitrophenyl chloroformate (2.42 g, 12 mmol, 1.5 eq), and TEA (3.3 ml, 24 mmol, 3 eq) were added to PEG solution at 4° C. (ice water), while taking precautions against moisture. Light yellow TEA hydrochloride salt was formed. After 15 minutes cooling bath was removed, and the reaction mixture was stirred at room temperature overnight. TLC showed (CHCl$_3$:MeOH:H$_2$O=90:18:2) that the reaction was complete. Solvent was evaporated. The residue was dissolved in ethyl acetate (~50° C.). TEA hydrochloride salt was filtered off and washed with warm ethyl acetate. Solvent was evaporated and the product recrystallized with isopropanol (three times). Yield: 38.2 g (92%). $^1$H NMR (DMSO-d$_6$, 360 MHz) δ 3.55 (s, PEG, 450H); 4.37 (t, PEG-CH$_2$, 2H); 7.55 (d, C$_6$H$_5$, 2H); 8.31 (d, C$_6$H$_5$, 2H).

1-Amino-2-propanol (1.1 ml, 14.52 mmol, 3 eq), and TEA (2.02 ml, 14.52 mmol, 3 eq) were added to mPEG (5K)-nitrophenyl carbonate (25 g, 4.84 mmol) in DMF (60 ml) and CH$_2$Cl$_2$ (40 ml). It was a yellow clear solution. The reaction mixture was stirred at room temperature for 30 minutes. TLC (CHCl$_3$:MeOH=90:10) showed that the reaction went to completion. Solvent (dichloromethane) was evaporated. Isopropanol (250 ml) was added to the product mixture in DMF (60 ml). Product precipitated immediately, and then recrystallized with iPrOH (three times). Yield: 22.12 g (90%). $^1$H NMR (DMSO-d$_6$, 360 MHz) δ 0.98 (d, CH$_3$CH(OH)CH$_2$, 3H); 3.50 (s, PEG, 180H); 4.03 (t, PEG-CH$_2$, 2H); 4.50 (d, CH$_3$CHOH, 1H); 7.0 (t, mPEG-OCONH).

mPEG(5K)-urethane-2-methyl propanol (22.12 g, 4.34 mmol) was dried azeotropically with toluene (45 ml). Dichloromethane (60 ml) was added to it. Methane sulfonyl chloride (604.6 μl, 7.81 mmol, 1.8 eq) and TEA (3.93 ml, 28.21 mmol, 6.5 eq) were added to mPEG-solution at 0° C. while maintaining stirring and taking precautions against moisture. After 30 minutes, cooling bath was removed, and the reaction mixture was stirred at room temperature for 16 h. Solvent was evaporated. Ethyl acetate was added to remove TEA salts. The product was recrystallized with isopropanol (three times). Yield: 20.27 g (90%). $^1$H NMR (DMSO-d$_6$, 360 MHz) 67 1.27 (d, CH$_3$CHOSO$_2$CH$_3$, 3H); 3.162 (s, CH$_3$O$_2$SOCH, 3H); 3.50 (s, PEG, 180H); 4.07 (t, PEG-CH$_2$, 2H); 4.64 (q, CH$_3$CHOH, 1H); 7.43 (t, mPEG-OCONH).

mPEG(5K)-urethane-2-methyl-methane sulfone (10.27 g, 1.98 mmol) was dried azeotropically with toluene (20 ml, each time). Sodium hydride (377 mg, 9.4 mmol, 4.75 eq) was added in anhydrous toluene (60 ml) at 0° C. (in ice water). After 5 minutes, triphenylmethanethiol (3.92 g, 14.6 mmol, 7.15 eq) was added to the solution. After 10 minutes, mPEG-urethane-2-methyl-methane sulfone (10.27 gm, 1.98 mmol) was added to the reaction mixture. It became a yellow solution. After 45 minutes, TLC (CHCl$_3$:MeOH:H$_2$O=90:18:2) showed that the reaction went to completion. Acetic acid (445.57 μl, 7.42 mmol, 3.75 eq) was added to the reaction mixture to neutralize excess of sodium hydride. The solution became thick and whitish. Solvent was evaporated and the solid was recrystallized with ethyl acetate (30 ml) and isopropanol (70 ml). The product mixture did not dissolve completely, while precipitate filtered off. Then the product mixture was recrystallyzed with isopropanol/tert-butyl alcohol (100 ml/20 ml). Yield: 8.87 g (84%). $^1$H NMR (DMSO-d$_6$, 360 MHz) δ 0.74 (d, CH$_3$CHSC(C$_6$H$_5$)$_3$, 3H), 3.50 (s, PEG, 180H), 4.0 (t, PEG-CH$_2$, 2H), 4.64 (q, CH$_3$CHOH, 1H); 7.49 (t, mPEG-OCONH); 7.20-7.41 (m, SC(C$_6$H$_5$)$_3$, 15H).

mPEG(5K)-urethane-2methyl-triphenylmethanethiol (8.87 g, 1.65 mmol) was dissolved in TFA/CH$_2$Cl$_2$(10 ml/10 ml) at 0° C. Under vigorous stirring, methoxy carbonylsulfenyl chloride (185.5 μl, 1.99 mmol, 1.2 eq) was added to the solution. The reaction mixture was stirred at room temperature for 15 minutes. TLC (CHCl$_3$:MeOH=90:10) showed that the reaction was complete. Solvents were evaporated. The product mixture was recrystallized with isopropanol:tert-butyl alcohol (80 ml:20 ml) two times. Tertiary butanol (5 ml) was added to the product, which was then lyophilized and dried in vacuo over P$_2$O$_5$ to give product as white fluffy solid (8.32 g, 97% yield). $^1$H NMR (DMSO-d$_6$, 360 MHz) δ 1.17 (d, CH$_3$CHSSCOOCH$_3$, 3H); 3.42 (s, PEG, 180H); 3.84 (s, CH$_3$OCOSSCH, 3H); 4.05 (t, mPEG-CH$_2$, 2H); 7.38 (t, mPEG-OCONH, 1H).

mPEG(5K)-urethane ethyl(methyl)dithiocarbonyl methoxide (8.32 g, 1.6 mmol) was dissolved in dry methanol (20 ml), and chloroform (2.5 ml). A solution of mercapto benzyl alcohol (592 mg, 4 mmol, 2.5 eq) in dry methanol (2 ml) was added to the PEG-solution. The reaction mixture was stirred at room temperature for 18 h. The solvent was evaporated and the product mixture was is recrystallized with ethyl acetate/isopropanol, 30 ml/100 ml (3 times). NMR showed ~16% product was formed. So, another portion of mercapto benzyl alcohol (322 mg, 2.18 mmol, 1.8 eq) in MeOH (2 ml) was added dropwise to the product mixture in MeOH/CHCl$_3$ (24 ml/l ml) at 0° C. (ice water). After addition (~10 minutes) completion, ice bath was removed, and the reaction mixture was stirred at room temperature for 24 h. TLC (CHCl$_3$:MeOH:H$_2$O=90:18:2) showed that the reaction was complete. Solvent was evaporated, and then product mixture was recrystallized with ethyl acetate/isopropanol, 30 ml/100 ml. Yield: 7.25 g, (94%). $^1$H NMR (DMSO-d$_6$, 360 MHz) δ 1.56 (d, CH$_3$CHSSC$_6$H$_5$CH$_2$OH, 3H); 3.29 (CH$_3$O-PEG, 3H); 3.50 (s, PEG, 450H); 4.03 (t, mPEG-CH$_2$, 2H); 4.46 (d, HOCH$_2$C$_6$H$_5$, 2H); 5.16 (t, HOCH$_2$C$_6$H$_5$, 1H); 7.30 (d, C$_6$H$_5$, 2H); 7.40 (br t, mPEG-OCONH, 1H); 7.50 (d, C$_6$H$_5$, 2H).

mPEG(5K)-urethane-ethyl(methyl)-dithiobenzyl alcohol (6.75 g, 1.27 mmol) was dissolved in CHCl$_3$ (30 ml), P-nitrophenyl chloroformate (513 mg, 2.54 mmol, 2 eq) was added to it at 0° C. (ice water). After 5 minutes triethylamine (531 µl, 3.81 mmol, 3 eq) was added. After 30 minutes ice bath was removed, and the reaction mixture was stirred at room temperature overnight. Solvent was evaporated. The product mixture was dissolved in ethyl acetate. TEA salt was filtered off, and then solvent was evaporated. Then the product mixture was recrystallized with ethyl acetate/isopropanol, 30 ml/100 ml (three times). Yield: 6.55 g (94%). $^1$H NMR (DMSO-d$_6$, 360 MHz) 67 1.17 (d, CH$_3$CHSSC$_6$H$_5$, 3H); 3.24 (CH$_3$O-PEG, 3H); 3.40 (s, PEG, 180H); 4.03 (br t, mPEG-CH$_2$, 2H); 5.28 (S, C$_6$H$_5$CH$_2$OCO, 2H); 7.45-8.35 (m, C$_6$H$_5$)$_2$, 8H)

mPEG-MeDTB-nitrophenylcarbonate (766 mg, 0.14 mmol, 1.29 eq) was dissolved in CHCl$_3$ (5 ml). DSPE (70 mg, 0.093 mol) and TEA (58.5 µl, 0.42 mmol, 4.5 eq) were added to PEG-solution, and was stirred at 50° C. (oil bath temp). After 20 minutes, TLC showed that the reaction didn't go to completion. More mPEG-MeDTB-nitrophenylcarbonate (total 1239 mg, 0.23 mmol, 2.47 eq) and 1-hydroxybenztriazole (HOBt) (25 mg, 0.19 mmol, 2 eq) were added. After 20 minutes, TLC (CHCl$_3$:MeOH:H$_2$O=90:18:2, with molybdenum and ninhydrin) showed that the reaction was complete. Solvent was evaporated. Product mixture was dissolved in warm (42° C.) ethyl acetate. It was a cloudy solution (TEA salt precipitated). The solution was filtered, and solvent was evaporated. MeOH, and 2 g of C8 silica was added to the product mixture. Solvent was evaporated again. Product containing C8 silica was added on the top of the column, and was eluted with MeOH:H$_2$O gradient (pressure), MeOH:H$_2$O 30:70, 100 ml; MeOH H$_2$O 50:50, 100 ml; MeOH H$_2$O 70:30, 250 ml (starting material eluted); MeOH H$_2$O 75:25=40 ml; MeOH H$_2$O 80:20, 200 ml (product eluted); MeOH=100 ml; CHCl$_3$:MeOH:H$_2$O=90:18:2, 100 ml; CHCl$_3$:MeOH H$_2$O=75:36:6, 100 ml. Fractions containing pure product were combined and evaporated to give product as colorless thick liquid. Tertiary butanol (5 ml) was added to it, lyophilized and then dried in vacuo over P$_2$O$_5$ to give product as white fluffy solid (467 mg, 83% yield). $^1$H NMR (DMSO-d$_6$, 360 MHz) δ 0.83 (d, 2(CH$_3$), 3H); 1.16 (d, CH$_3$CHSSC$_6$H$_5$, 3H); 1.21 (s, 28(CH$_2$, 56H); 1.47 (br m, CH$_2$CH$_2$CO, 4H); 2.23 (2×t, CH$_2$CH$_2$CO, 4H); 3.50 (s, PEG, 180H); 4.04 (br t, mPEG-CH$_2$, 2H); 4.05 (trans d, PO$_4$CH$_2$CHCH$_2$, 1H); 4.24 (cis d, PO$_4$CH$_2$CHCH$_2$, 1H); 4.97 (s, C$_6$H$_5$CH$_2$OCO-DSPE, 2H); 5.03 (br s, (PO$_4$CH$_2$CH, 1H); 7.32 (d, C$_6$H$_5$, 2H); 7.53 (d, C$_6$H$_5$, 2H); 7.52 (br s, mPEG-OCONH, 1H). MALDI-TOFMS produced a bell shaped distribution of ions spaced at equal 44 Da intervals, corresponding to the ethylene oxide repeating units. The average molecular mass of the conjugate and mPEG-thiol (mostly cleaved disulfide) is 6376 and 5368 Da (theoretical molecular mass ~6053, and 5305 Daltons).

B. mPEG-ethylDTB-DSPE mPEG-urethane ethyl(ethyl)dithiocarbonyl methoxide (2 g, 0.90 mmol) was dissolved in dry methanol (8 ml). At the beginning the solution was cloudy, but after 5 minutes it became a clear solution. Mercaptobenzyl alcohol (265.2 mg, 1.79 mmol, 2 eq) was added to the PEG-solution. The reaction mixture was stirred at room temperature for 30 hours. Ether (70 ml) was added to the reaction solution to precipitate the product, and kept at 4° C. overnight. The white solid was filtered and recrystallized with ethyl acetate/ether, 30 ml/70 ml. Yield: 1.96 g, (94%). $^1$H NMR (DMSO-d$_6$, 360 MHz) δ0.86 (d, CH$_3$CH$_2$CHSSC$_6$H$_5$CH$_2$OH, 3H); 1.42 (p, CH$_3$CH$_2$CHSSC$_6$H$_5$CH$_2$OH, 1H); 1.64 (p, CH$_3$CH$_2$CHSSC$_6$H$_5$CH$_2$OH, 1H); 3.51 (s, PEG, 180H); 4.03 (t, mPEG-CH$_2$, 2H); 4.47 (d, HOCH$_2$C$_6$H$_5$, 2H); 5.20 (t, HOCH$_2$C$_6$H$_5$, 1H); 7.31 (d, C$_6$H$_5$, 2H); 7.42 (br t, mPEG-OCONH, 1H); 7.49 (d, C$_6$H$_5$, 2H).

N-hydroxy-s-norbornene-2,3-dicarboxylic acid imide (HONB) (48 mg, 0.269 mmol) was added to DSPE (55 mg, 0.073 mmol) in CHCl$_3$ (3 ml) at 50° C. (oil bath temperature). After 3-4 minutes it became a clear solution. Then mPEG-EtDTB-nitrophenylchloroformate (334 mg, 0.134 mmol) was added, followed by triethylamine (TEA, 45 µl, 0.329 mmol). After 20 minutes TLC (CHCl$_3$:MeOH:H$_2$O=90:18:2) showed that the reaction went to completion (molybdenum and ninhydrin sprays). Solvent was evaporated. Product mixture was dissolved in methanol, mixed with C8 silica (1 g) and striped of the solvent by rotary evaporation. The solid residue was added on the top of the C8-column, which was then eluted with MeOH:H$_2$O gradient (pressure), MeOH:H$_2$O=30:70, 60 ml; MeOH:H$_2$O=50:50, 60 ml; MeOH:H$_2$O=70:30, 140 ml; MeOH:H$_2$O=75:25=140 ml (starting material eluted); MeOH:H$_2$O=80:20, 80 ml; MeOH:H$_2$O=90:10, 140 ml (product eluted); MeOH=40 ml; CHCl$_3$:MeOH:H$_2$O=90:18:10, 40 ml. Fractions containing pure product were combined and evaporated to give product as colorless thick liquid. Tertiary butanol (5 ml) was added, lyophilized and then dried in vacuo over P$_2$O$_5$ to give product as white fluffy solid (175 mg, 78% yield). $^1$H NMR (DMSO-d$_6$, 360 MHz) δ 0.85 (d, 2(CH$_3$), 6H; d, CH$_3$CHSSC$_6$H$_5$, 3H); 1.22 (s, 28(CH$_2$), 56H); 1.49 (br m, CH$_2$CH$_2$CO, 4H); 2.24 (2×t, CH$_2$CH$_2$CO, 4H); 3.50 (s, PEG, 180H); 4.04 (br t, mPEG-CH$_2$, 2H); 4.08 (trans d, PO$_4$CH$_2$CHCH$_2$, 1H); 4.27 (cis d, PO$_4$CH$_2$CHCH$_2$, 1H); 4.98 (s, C$_6$H$_5$CH$_2$OCO-DSPE, 2H); 5.06 (br s, (PO$_4$CH$_2$CH, 1H); 7.34 (d, C$_6$H$_5$, 2H); 7.53 (d, C$_6$H$_5$, 2H); 7.55 (br s, mPEG-OCONH, 1H).

Example 3

Synthesis of mPEG-DTB-nitrophenvichloroformate

This reaction scheme is illustrated in FIG. 5.

A. Procedures for Synthesis of 1-(mercaptomethyl)ethylammonium Chloride 1. 2-Amino-1-methylethyl hydrogen sulfate. 1-Amino-2-propanol (22.53 g, 0.3 mol) was vigorously stirred in an ice bath. Sulfuric acid (16.10 ml, 0.3 mol) was added very slowly, over the course of one hour. Thick vapors and a very viscous solution were formed in the flask. After addition was complete, the reaction was heated between 170° C. and 180° C., under reduced pressure, connected to the house vacuum. Upon heating, the reaction turned light brown. After all water was removed (approximately 1 hour) it was allowed to cool to room temperature. Upon cooling a brown, glassy solid was formed which would crystallize when triturated with methanol. It was dissolved in water (50 ml) at 60° C. Enough warm methanol was added to make the solution 80% methanol. Upon cooling, crystals formed which were then filtered and dried over $P_2O_5$. Yield: 17.17 g (37%). $^1$H NMR ($D_6$-DMSO): 67 1.16 (d, $CH_3$, 3H); δ 2.78 (dd, $NH_3$—$CH_2$, 1H) δ 2.97 (dd, $NH_3$—$CH_2$, 1H); δ 4.41 (m, CH—$OSO_3$, 1H); δ 7.69 (s, $H_3N$, 3H). Melting point: 248°-250° C. (lit: 250° C.)

2. 5-Methylthiazolidine-2-thione. 2-Amino-1-methylethyl hydrogen sulfate (23.03 g, 148 mmol) and carbon disulfide (10.71 ml, 178 mmol, 1.2 eq.) were stirred in a 250 ml round-bottom-flask in 50% aqueous ethanol (40 ml). To this, sodium hydroxide (13.06 g, 327 mmol, 2.2 eq.) in 50% aqueous ethanol (50 ml) was added drop-wise, very slowly. Upon addition of sodium hydroxide, all starting materials dissolved and the solution turned orange. The reaction was refluxed (85° C.) for 40 minutes, after which time it turned bright yellow and a thick precipitate was formed. Ethanol was evaporated and then the aqueous solution was warmed and then filtered through a Buchner funnel to remove all water-soluble impurities. The remaining crystals were dissolved in warm ethanol and then warm water was added until the solution was 80% water. The mixture was allowed to cool and then refrigerated, yielding long, needle-like crystals. Yield: 14.64 g (75%). $^1$H NMR ($D_6$-DMSO): δ 1.33 (d, $CH_3$, 3H); δ 3.50 (m, $R_3CH$, 1H); δ 3.95 (dd, N—$CH_2$, 1H); δ 4.05 (m, N—$CH_2$, 1H); δ 10.05 (s, NH, 1H). Melting point: 92.5-93.5 (lit: 94-95).

3. 1-(mercaptomethyl)ethylammonium chloride. 5-Methylthiazolidine-2-thione (6.5 g, 49 mmol) was placed in a 250 ml round-bottom-flask. A solution of aqueous hydrochloric acid (40 ml, 18% in $H_2O$) was added and the flask was heated in an oil bath. The reaction refluxed (120° C.) for one week. Three times throughout the week 1 ml of concentrated hydrochloric acid was added. The reaction was monitored using TLC with ethyl acetate as eluent. They were visualized using UV, ninhydrin, and iodine vapors. Through most of the week the reaction was a heterogeneous mixture, with the starting material as oil which was denser than water. After one week the oil starting material was gone, although still visible on TLC. The reaction was removed from heat and allowed to cool to room temperature, and then was refrigerated to crystallize starting material. The crystallized starting material was filtered. Filtrate was evaporated and it was dried over $P_2O_5$ and NaOH to remove all water and HCl. The crude product was washed with two portions of diethyl ether (50 ml each) to remove all starting material. It was again dried over $P_2O_5$. Yield: 2.83 g (45%). $^1$H NMR ($D_6$-DMSO): δ 1.33 (d, $CH_3$, 3H); δ 2.92 (m, N—$CH_2$, 2H); δ 3.12 (m, SH, 1H); δ 3.18 (m, $R_3$—CH, 1H); δ 8.23 (bs, $NH_3$, 3H). Melting point: 80-82° C. (lit: 92-94).

B. Synthesis of mPEG-ethyl-DTB-nitrophenylchloroformate 1. 2-Amino-1-ethylethyl hydrogen sulfate. 1-Amino-2-butanol (15 ml, 158 mmol) was vigorously stirred in a 100 ml round-bottom-flask in an ice bath. Sulfuric acid (8.43 ml, 158 mmol) was added very slowly, over the course of one hour. Thick vapors and a very viscous solution were formed in the flask. After addition was complete, the reaction was heated between 170° C. and 180° C., under reduced pressure, connected to the house vacuum. Upon heating, the reaction turned light brown. After all water was removed (approximately 1 hour) it was allowed to cool to room temperature. Upon cooling a brown, glassy solid was formed. It was dissolved in hot water (50 ml) and then placed in the refrigerator overnight. Upon cooling, crystals formed which were then filtered and dried over $P_2O_5$. Yield: 9.98 g (37%). $^1$H NMR ($D_6$-DMSO): δ 0.87 (t, $CH_3$, 3H); δ 1.51 (q, $CH_3$—$CH_2$, 2H); δ 2.82 (dd, $NH_3$—$CH_2$, 1H); δ 3.00 (dd, $NH_3$—$CH_2$, 1H); δ 4.21 (m, CH—$OSO_3$, 1H); δ 7.70 (s, $H_3N$, 3H).

2. 5-Ethylthiazolidine-2-thione. 2-Amino-1-ethyl-ethyl hydrogen sulfate (9.98 g, 59 mmol) and carbon disulfide (4.26 ml, 71 mmol, 1.2 eq.) were stirred in a 100 ml round-bottom-flask in 50% aqueous ethanol (15 ml). To this, sodium hydroxide (5.20 g, 130 mmol, 2.2 eq.) in 50% aqueous ethanol (20 ml) was added drop-wise, very slowly. Upon addition of sodium hydroxide, all starting materials dissolved and the solution turned orange. The reaction was refluxed (85° C.) for 40 minutes, after which time it turned bright yellow and a thick precipitate was formed. Ethanol was evaporated and then the aqueous solution was warmed and then filtered through a Buchner funnel to remove all water-soluble impurities. The remaining crystals were dissolved in warm ethanol and then warm water was added until the solution was 80% water. The mixture was allowed to cool and then refrigerated, yielding needle-like crystals. Yield: 7.28 g (86%). $^1$H NMR ($D_6$-DMSO): δ 0.88 (t, $CH_3$, 3H); δ 1.66 (in, $CH_3$—$CH_2$, 2H); δ 3.58 (m, $R_3CH$, 1H); δ 3.93 (m, N—$CH_2$, 2H); δ 10.06 (s, NH, 1H). Melting point: 76-78° C. (lit: 76.6-76.9).

3. 1-(mercaptoethyl)ethylammonium chloride. 5-Ethylthiazolidine-2-thione (7.24 g, 50 mmol) was placed in a 250 ml round-bottom-flask. A solution of aqueous hydrochloric acid (45 ml, 18% in $H_2O$) was added and the flask was heated in an oil bath. Upon heating, the starting material melted, forming, all heterogeneous mixture. The reaction refluxed (120° C.) for one week. Four times throughout the week 1 ml of concentrated hydrochloric acid was added. The reaction. was monitored using TLC with ethyl acetate as eluent. They were visualized using UV, ninhydrin, and iodine vapors. Throughout the week the reaction was a heterogeneous mixture, with the starting material as oil which was denser than water. The reaction was removed from heat and allowed to cool to room temperature, and then was refrigerated to crystallize starting is material. The crystallized starting material was filtered. Filtrate was evaporated and it was dried over $P_2O_5$ and NaOH to remove all water and HCl. The crude product was washed with two portions of diethyl ether (50 ml each) to remove all starting material. It was again dried over $P_2O_5$. Yield: 3.66 g (52%). $^1$H NMR ($D_6$-DMSO):

Example 4

Synthesis of mPEG-DTB-lipid

This reaction scheme is illustrated in FIG. 6A.

1,2-distereoyl-sn-glycerol (500 mg, 0.8 mmol) was dried azeotropically with benzene (3 times). Para-nitrophenyl chloroformate (242 mg, 1.2 mmol, 1.5 eq), dimethylaminopyridine (DMAP) (10 mg, 0.08 mmol, 0.1 eq), and TEA (334.5 μl, 2.4 mmol, 3 eq) were added to 1,2-distereoyl glycerol in $CHCl_3$ (5 ml). The reaction mixture was stirred at room temperature for 2 h. TLC (Toluene:ethyl acetate=7:3) showed that the reaction was complete. Then the product mixture was extracted with 10% citric acid to remove dimethylaminopyridine (DMAP), washed with acetonitrile (3 ml, 4 times) to remove excess of p-nitrophenyl chloroformate. Pure product was dried in vacuo over $P_2O_5$. Yield: 557 mg (88%). $^1$H NMR ($CHCl_3$, 360 MHz) δ 0.88 (t, end $CH_3$, 6H); 1.25 (s, 28×$CH_2$, 56H); 1.58 (m, $CH_2CH_2CO$, 4H); 2.34 (2×t, $CH_2CO$, 4H); 4.22 (trans d, $CH_2OCOC_{17}H_{35}$, 1H); 4.35 (m, $OCOOCH_2CH$, 2H); 4.51 (cis d, $CH_2OCOC_{17}H_{35}$, 1H); 5.37 (m, $OCOOCH_2CH$, 1H); 7.39 (d, $C_6H_5$, 2H); 8.28 (d, $C_6H_5$, 2H).

Ethylene diamine (42 μl, 0.63 mmol, 5 fold excess), and pyridine (200 μl, were added in $CHCl_3$ (1 ml). 2-disteroylsn-p-nitrophenyl carbonate (100 mg, 0.13 mmol) was dissolved in $CHCl_3$(1 ml) and added dropwise to ethylene diamine solution with a Pasteur pipette at 0° C. (ice water) and continued overnight (16 h). TLC ($CHCl_3$:MeOH:$H_2O$ 90:18:2, and $CHCl_3$:MeOH=90:10) showed that the reaction was complete. Solvent was evaporated to remove pyridine. Then the product mixture was dissolved in $CHCl_3$, loaded onto the column (Aldrich, Silica gel, 60° A, 200-400 mesh), and eluted with $CHCl_3$:$CH_3COCH_3$, and $CHCl_3$:MeOH gradient, $CHCl_3$:$CH_3COCH_3$=90:10, 60 ml (upper spot eluted); $CHCl_3$:NeOH=90:10, 60 ml (product eluted). Fractions containing pure product were combined and evaporated. Tert-butanol was added and dried in vacuo over $P_2O_5$. Yield: 64 mg (75%). $^1$H NMR (DMSO-$d_6$, 360 MHz) δ 0.83 (t, end $CH_3$, 6H); 1.22 (s, 28×$CH_2$, 56H); 1.51 (m, $CH_2CH_2CO$, 4H); 2.25 (2×t, $CH_2CO$, 4H); 2.83 (m, $H_2NCH_2CH_2NH$, 2H); 3.21 (m, $H_2NCH_2CH_2NH$, 2H); 4.10-4.14 (m & cis d, $COOCH_2CHCH_2$, 4H); 5.17 (m, $OCOOCH_2CH$, 1H); 7.78 (m, $H_2NCH_2CH_2NH$, 2H).

mPEG-MeDTB-nitrophenylchloroformate (400 mg, 0.162 mmol, 2.2 eq) was dissolved in $CHCl_3$ in (2 ml). 1,2-steroyl-sn-ethylene amine (51 mg, 0.075 mmol) and TEA (37 µl, 0.264 mmol, 3.52 eq) were added to the solution. Then the reaction mixture was stirred at 45° C. for 20 minutes. TLC ($CHCl_3$:MeOH:$H_2O$=90:18:2, and $CHCl_3$:MeOH=90:10) showed that the reaction went to completion. Solvent was evaporated. The product mixture was dissolved in methanol. 2 g of C8 silica was added and then solvent was evaporated. C8 silica containing product mixture was added on the top of the C8 column ((Supelco, Supel clean. Lot no. SP0824), and was eluted with MeOH:$H_2O$ gradient (pressure), MeOH:$H_2O$=60:40, 40 ml; MeOH:$H_2O$=70:30, 80 ml (starting material eluted); MeOH:$H_2O$=80:20, 40 ml; MeOH:$H_2O$=90:10=20 ml; $CHCl_3$:MeOH:$H_2O$=5:80:15, 20 mi; $CHCl_3$:MeOH:$H_2O$=90:18:10, 40 ml (product eluted). Fractions containing pure product were combined and evaporated to give product as colorless thick liquid. Tertiary butanol (5 ml) was added and the solution was lyophilized and then dried in vacuo over $P_2O_5$ to give product as white solid (200 mg, 89% yield). $^1$H NMR (DMSO-$d_6$, 360 MHz) δδ 0.83 (t, end $CH_3$, 6H); 1.22 (s, 28×$CH_2$, 56H); 1.48 (m, $CH_2CH_2CO$, 4H); 2.25 (2×t, $CH_2CO$, 4H); 3.10 (m, $HNCH_2CH_2NH$, 4H); 3.50 (s, PEG, 180H); 4.04 (t, mPEG-$CH_2$, 2H); 4.09 (trans d, $COOCH_2CHCH_2$, 1H); 4.25 (cis d, $COOCH_2CHCH_2$, 1H); 4.98 (s, $C_6H_5CH_2OCO$, 2H); 5.23 (m, $COOCH_2CHCH_2$, 1H); 7.18 (m, $NHCH_2CH_2NH$, 2H); 7.33 (d, $C_6H_5$, 2H); 7.38 (m, mPEG-OCONH, 1H); 7.52 (d, $C_6H_5$, 2H).

Example 5

Preparation of Liposomes Containing Nucleic Acid

Liposomes were prepared by preparing a solution of dioleoyltrimethylammonium-propane (DOTAP) and cholesterol (Chol) in a ratio of 55:45. The liposomes were then mixed with DNA at a ratio of 14 nmole lipids per µg DNA. The complex was sized ≈150 nm diameter. DNA-liposome complexes were incubated with micellar solutions of mPEG-DSPE, mPEG-Me-DTB-DSPE, or mPEG-H-DTB-DSPE, with or without a folate targeting ligand, for 1 hour at room temperature to achieve insertion of the PEG-lipid into the pre-formed liposomes.

A pNSL plasmid encoding for luciferase was constructed as described in U.S. Pat. No. 5,851,818 from two commercially available plasmids, pGFP-N1 plasmid (Clontech, Palo Alto, Calif.) and pGL3-C (Promega Corporation, Madison, Wis.). The luciferase reporter plasmid DNA solution was added to the acidic liposome solution slowly with continuous stirring for 10 minutes.

Folate ligands were conjugated to amino-PEG-DSPE according to procedures known in the art (Gabizon, A. et al, *Bioconjugate Chem.*, 10:289 (1999)). DNA-liposome complexes were incubated with micellar solutions of mPEG-DSPE or folate-PEG-DSPE with continuous stirring for 20 minutes to achieve insertion of the ligand-PEG-lipid into the pre-formed liposomes resulting in approximately 30 folate ligands per liposome.

Example 6

In vitro Transfection of Luciferase in a BHK Cell Line

A BHK cell line was transfected by complexes containing luciferase reporter gene prepared as described in Example 5. Cells were cultured in normal or folic acid-free RPMI medium, with 10% fetal bovine serum, L-glutamine, penicillin, and streptomycin. Prior to transfection, the cell culture was rinsed with phosphate-buffered saline (PBS). $1 \times 10^3$ cells were incubated with the complex (1 ml DNA-liposome complex) for 2 hours at 37° C. in a 5% CO2 is incubator. After incubation, 4.0 ml of complete or folic acid-free RPMI 1640 cell medium was added to the cell culture. The cells were harvested and assayed for luciferase assay.

After 2 hours of incubation in the PBS, all of the cells were spherical and floating and the appearance of the cells remained unchanged and the cells remained attached to the flask. Complete media was added on top of the complex to recover the cells.

Liposomes were formed as detailed in Example 5 with the following lipid components:

| No. | Formulation |
|---|---|
| 1 | 54.7% DOTAP |
|   | 44.8% Cholesterol |
|   | 0.5% $PEG_{2000}$-DSPE |
| 2 | 54.7% DOTAP |
|   | 44.8% Cholesterol |
|   | 0.5% Folate-$PEG_{2000}$-DSPE |
| 3 | 53.9% DOTAP |
|   | 44.1% Cholesterol |
|   | 2.0% $PEG_{2000}$-DSPE |
| 4 | 54.7% DOTAP |
|   | 44.8% Cholesterol |
|   | 2.0% Folate-$PEG_{2000}$-DSPE |
| 5 | 52.25% DOTAP |
|   | 42.75% Cholesterol |
|   | 5.0% $PEG_{2000}$-DSPE |
| 6 | 52.25% DOTAP |
|   | 42.75% Cholesterol |
|   | 5.0% Folate-$PEG_{2000}$-DSPE |
| 7 | 54.7% DOTAP |
|   | 44.8% Cholesterol |
|   | 0.5% PEG-Me-DTB-DSPE |
| 8 | 54.7% DOTAP |
|   | 44.8% Cholesterol |
|   | 5.0% Folate-PEG-Me-DTB-DSPE |
| 9 | 53.9% DOTAP |
|   | 44.1% Cholesterol |
|   | 2.0% PEG-Me-DTB-DSPE |
| 10 | 53.9% DOTAP |
|   | 44.1% Cholesterol |
|   | 2.0% Folate-PEG-Me-DTB-DSPE |
| 11 | 52.25% DOTAP |
|   | 42.75% Cholesterol |
|   | 5.0% PEG-Me-DTB-DSPE |

-continued

| No. | Formulation |
|---|---|
| 12 | 52.25% DOTAP |
|  | 42.75% Cholesterol |
|  | 5.0% Folate-PEG-Me-DTB-DSPE |
| 13 | 54.7% DOTAP |
|  | 44.8% Cholesterol |
|  | 0.5% PEG-H-DTB-DSPE |
| 14 | 54.7% DOTAP |
|  | 44.8% Cholesterol |
|  | 0.5% Folate-PEG-H-DTB-DSPE |
| 15 | 53.9% DOTAP |
|  | 44.1% Cholesterol |
|  | 2.0% PEG-H-DTB-DSPE |
| 16 | 53.9% DOTAP |
|  | 44.1% Cholesterol |
|  | 2.0% Folate-PEG-H-DTB-DSPE |
| 17 | 52.25% DOTAP |
|  | 42.75% Cholesterol |
|  | 5.0% PEG-H-DTB-DSPE |
| 18 | 52.25% DOTAP |
|  | 42.75% Cholesterol |
|  | 5.0% Folate-PEG-H-DTB-DSPE |
| 19 | 55% DOTAP |
|  | 44% Cholesterol |
| 20 | lipofectamine |

Example 7

In vitro Transfection of Luciferase in a KbHiFr Cell Line

KB cells, a human nasopharyngeal epidermal carcinoma (Saikawa, Y., *Biochemistry*, 34:9951-9961 (1995)), were grown in low folic acid medium to obtain cells over-expressing folic acid receptors, KB-HiFR cells. Cells were cultured in normal or folic acid-free RPMI medium, with 10% fetal bovine serum, glutamine 2 mM, penicillin 50 u/mL, and streptomycin 50 μg/mL. The concentration of folic acid in the serum-containing folic acid-free medium is only 3 nM, as opposed to 2.26 μM (1 mg/L) under normal culture conditions. Cells were routinely passed by treatment with trypsin (0.05%)-EDTA (0.02%) solution in Industries (Beyt Haernek, Israel), and fetal bovine serum was from GIBCO (Grand Island, N.Y.).

The KB-HiFr cell line was transfected by complexes containing luciferase reporter gene as described in Example 6. The cells were harvested and assayed for luciferase and protein assay at 24 hours after transfection. The samples for protein assay were diluted 10-fold prior to analysis.

Example 8

In vitro Transfection of Luciferase in a BHK Cell Line in the Presence of Cysteine A BHK cell line was transfected by complexes containing luciferase reporter gene. Cells were cultured in RPMI medium, with 10% fetal bovine serum, L-glutamine, penicillin, and streptomycin.

Liposomes were formed as detailed in Example 5 with the lipid components 52.8% DOTAP, 43.2% Cholesterol, and 4% $PEG_{2000}$, PEG-Me-DTB-DSPE, or PEG-H-DTB-DSPE. The complexes were prepared as described in Example 5 and stored overnight at 4° C. The next day, 3.2 ml of cysteine in PBS at a concentration of 50, 250, or 1250 μM was added to the complex and mixed by inversion to form a suspension.

Prior to transfection, the cell culture was rinsed with phosphate-buffered saline (PBS). $1 \times 10^3$ cells were incubated with the complex (1 ml DNA-liposome complex) for 2 hours at 37° C., in a 5% $CO_2$ incubator. After 24 hours, the cells were harvested and assayed for luciferase and protein.

Example 9

Cleavable Lipopolymer Cleavage Assay

Liposomes were prepared essentially as described in Example 5 using unilamellar liposomes (≈100 nm) composed of DOPE:mPEG-DTB-DSPE in a 100:3 molar ratio. Fluorophores (p-xylene-bis-pyridinium bromide, trisodium 8-hydroxy-pyrenetrisulfonate) were entrapped in the liposomes. As DOPE prefers the hexagonal phase, the entrapped fluorophores were released in response to PEG cleavage. Cysteine, at concentrations of 15 μM, 75 μM, 150 μM, 300 μM, 1500 μM, 3000 μM, and 15000 μM, was added to the liposomes and release of the fluorophores was assayed.

Example 10

Preparation of Neutral Cationic Lipid

A. Preparation of Para-nitrophenyl Carbonate of Distearoyl Glycerol

As illustrated in FIG. 1, 1,2-distearoyl-sn-glycerol (500 mg, 0.8 mmol; Compound I) was dried azeotropically with benzene (3 times with rotary evaporator). Para-nitrophenyl chloroformate (242 mg, 1.2 mmol, 1.5 eq; Compound II), 4-dimethylaminopyridine (10 mg, 0.08 mmol, 0.1 eq), and triethylamine (334 μl, 204 mmol, 3 eq) were added to 1,2-distearoyl glycerol in $CHCl_3$ (5 ml). The reaction mixture was stirred at room temp for 2 h. TLC showed that the reaction was complete. The mixture was diluted with $CHCl_3$ (50 ml) and extracted with 10% citric acid (3×15 mL). The organic layer was dried ($MgSO_4$) and evaporated to give a solid. The solid (light orange) was washed with acetonitrile (4×3 mL) to remove excess of p-nitrophenyl chloroformate. The product, para-nitrophenyl carbonate of distearoyl glycerol (Compound III), was dried under vacuum over $P_2O_5$. Yield: 557 mg (88%). $^1H$ NMR (360 MHz, DMSO-D6,): δ 0.88 (t, $CH_3$, 6H); 1.26 (s, $CH_2$ 58H); 1.62(m, $CH_2CH_2CO$, 4H); 2.4 (2×t, $CH_2CO$, 4H); 4.2 (dd, trans $CH_2OCO$, 1H); 4.35 (m, $CH_2OCOO$, 2H); 4.5 (dd, cis $CH_2OCO$, 1H); 5.38 (m, $CH_2CHCH_2$, 1H); 7.4 (d, $C_6H_5$, 2H);8.3 (d, $C_6H_5$, 2H).

B. Preparation of Carbamate of Histamine and Distearoyl Glycerol

Para-nitrophenyl carbonate of 1,2-distearoyl glycerol (350 mg, 0.44 mmol, Compound III) was added to Histamine (46 mg, 0.40 mmol, 0.9 eq; Compound IV) in $CHCl_3$ (1 ml) with DMSO (200 μl). Pyridine (300 μl; Compound V) was added to the solution. The reaction mixture was stirred at room temperature overnight (~20 h). TLC ($CHCl_3$:MeOH=90:10) showed that the reaction was complete. Solvent was evaporated. The product (Compound VI) was dissolved in $CHCl_3$, poured on to silica gel (Aldrich, 230-400 mesh, 60 Å) column, and eluted with following solvents, $CHCl_3$:$CH_3COCH_3$=90:10, 40 ml (upper spot eluted); $CHCl_3$:IPA=80:20, 40 ml (product eluted); $CHCl_3$:IPA=70:30, 40 ml (more product eluted). Fractions containing pure product were combined, and evaporated. The product was dried under vacuo over $P_2O_5$ and was obtained as white solid (236 mg, 80% yield). $^1H$ NMR (360 MHZ, $CDCl_3$/MeOH=1:1 with TMS):δ 0.88(t, CH3, 6H.); 1.28 (s,$CH_2$,56H; 1.62 (m, $CH_2CH_2CO$, 4H); 2.34 (2×t, $CH_2CO$, 4H); 2.77 (t, CH$_2$CH$_2$NH, 2H); 3.18 (t, CH$_2$CH$_2$CO, 2H); 4.05-4.2 (dd, cis and trans CH$_2$CHCH$_2$, 4H); 5.13 (m, CH$_2$CHCH$_2$, 1H); 608 (s, Histamine, 1H); 7.53 (s, Histamine, 1H).

What is claimed is:

1. A composition for transfecting a host cell with a gene, comprising:
a complex comprised of (i) liposomes comprised of a cationic lipid and a vesicle-forming lipid derivatized with a hydrophilic polymer and (ii) a nucleic acid having a selected gene for transfection, wherein said lipid-derivatized polymer has the general structure:

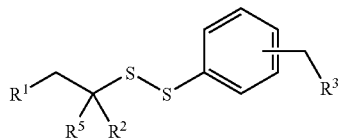

wherein R$^1$ is the hydrophilic polymer comprising a linkage for attachment to the dithiobenzyl moiety; R$^2$ and R$^5$ are independently selected from the group consisting of H, alkyl and aryl; R$^3$ is selected from the group consisting of O(C=O) R$^4$, S(C=O) R$^4$, and O(C=S) R$^4$; where R$^4$ is the vesicle-forming lipid; and where orientation of CH$_2$—R$^3$ is selected from the ortho position and the para position.

2. The composition of claim 1, wherein said vesicle-forming lipid R$^4$ is an amine-containing lipid.

3. The composition of claim 2, wherein said lipid has a single hydrocarbon tail or a double hydrocarbon tail.

4. The composition of claim 3, wherein said lipid is a phospholipid.

5. The composition of claim 1, wherein R$^2$ and R$^5$ are alkyls.

6. The composition of claim 1, wherein R$^1$ is selected from the group consisting of polyvinylpyrrolidone, polyvinylmethylether, polymethyloxazoline, polyethyloxazoline, polyhydroxypropyloxazoline, polyhydroxypropyl-methacaylamide, polymethacrylamide, polydimethyl-acrylamide, polyhydroxypropylmethacrylate, podroxyethylacrylate, hydroxymethylceiiuiose, hydroxyethylceiiulose, polyethyleneglycol, polyaspartamide, copolymers thereof, and polyethyleneoxlde-polypropylene oxide.

7. The composition of claim 1, wherein R$^1$ is polyethyleneglycol.

8. The composition of claim 7, wherein R$^5$ is H and R$^2$ is CH$_3$ or C$_2$H$_5$.

9. The composition of claim 1, wherein said catlonic lipid is seiected from the group consisting of dimethyldloctadecylammonium (DDAB), 1,2-diolelyloxy-3-(trimethylamino) propane (DOTAP), N-[1-(2,3,-dltstradecyloxy)propyl]-N,N-dimeth-yl-N-hydroxyethylammonium bromide (DMRIE), N-[1-(2,3,-dioleyloxy)propyl]-N,N-dimethyl-N-hydroxy ethylammonium bromide (DORIE), N-[1-(2,3-dioleyloxy) propyl]-N,N,N-trimethylammonium chloride (DOTMA), dioleoylphosphatidylethanolamine (DOPE), and 3β[N-(N', N'-dimethylaminoethane) carbamoyl] cholesterol (DC-Chol).

10. The composition of claim 1, wherein said liposomes further include cholesterol.

11. The composition of claim 1, wherein said nucleic acid is DNA or RNA.

12. The composition of claim 1, wherein said nucleic acid is a plasmid.

13. The composition of claim 1, where said gene encodes for a protein selected from the group consisting of Factor VIII, cytokines, p53, and HSV-tk.

14. A method for preparing a liposome/nucleic acid complex, comprising,
preparing a complex comprised of (i) liposomes comprised of a cationic lipid and a vesicle-forming lipid derivatized with a hydrophilic polymer, said hydrophilic polymer covalently linked to said vesicle-forming lipid by a releasable linkage and (ii) a nucleic acid having a selected gene for transfection,
wherein said lipid-derivatized polymer has the general structure:

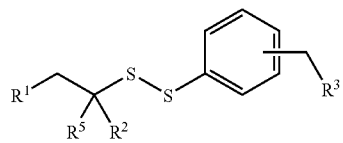

wherein R$^1$ is the hydrophilic polymer comprising a linkage for attachment to the dithiobenzyl moiety; R$^2$ and R$^5$ are independently selected from the group consisting of H, alkyl and aryl; R$^3$ is selected from the group consisting of O(C=O) R$^4$, S(C=O) R$^4$, and O(C=S) R$^4$; R$^4$ is the vesicle-forming lipid; and where orientation of CH$^2$—R$^3$ is selected from the ortho position and the para position.

15. The method of claim 14, wherein said vesicle-forming lipid R$^4$ is an amine-containing lipid.

16. The method of claim 15, wherein said lipid has a single hydrocarbon tail or a double hydrocarbon tail.

17. The method of claim 15, wherein said lipid is a phospholipid.

18. The method of claim 14, wherein R$^2$ and R$^5$ are alkyls.

19. The method of claim 14, wherein R$^1$ is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

20. The method of claim 14, wherein R$^1$ is polyethyleneglycol.

21. The method of claim 20, wherein R$^5$ is H and R$^2$ is CH$_3$ or C$_2$H$_5$.

* * * * *